US009750416B2

(12) United States Patent
Liao et al.

(10) Patent No.: US 9,750,416 B2
(45) Date of Patent: Sep. 5, 2017

(54) SYSTEM AND METHOD FOR DETECTION OF PULMONARY EMBOLISM

(75) Inventors: Wangcai Liao, Cary, NC (US); Jeffrey Stahmann, Ramsey, MN (US); Bin Mi, Plymouth, MN (US); Yunlong Zhang, Mounds View, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1118 days.

(21) Appl. No.: 13/438,682

(22) Filed: Apr. 3, 2012

(65) Prior Publication Data

US 2012/0190992 A1 Jul. 26, 2012

Related U.S. Application Data

(63) Continuation of application No. 12/414,465, filed on Mar. 30, 2009, now Pat. No. 8,147,415.

(60) Provisional application No. 61/126,860, filed on May 7, 2008.

(51) Int. Cl.

| A61B 5/02 | (2006.01) |
|---|---|
| A61B 5/0215 | (2006.01) |
| A61B 5/08 | (2006.01) |
| A61B 5/00 | (2006.01) |
| A61B 5/021 | (2006.01) |

(52) U.S. Cl.
CPC ........ *A61B 5/0215* (2013.01); *A61B 5/02007* (2013.01); *A61B 5/02108* (2013.01); *A61B 5/08* (2013.01); *A61B 5/412* (2013.01); *A61B 5/6846* (2013.01); *A61B 5/7275* (2013.01)

(58) Field of Classification Search
CPC ... A61B 5/02007; A61B 5/0215; A61B 5/412; A61B 5/6846; A61B 5/08; A61B 5/021; A61B 5/042
See application file for complete search history.

(56) References Cited

U.S. PATENT DOCUMENTS

| 4,562,841 A | 1/1986 | Brockway et al. |
|---|---|---|
| 4,928,688 A | 5/1990 | Mower |
| 5,036,849 A | 8/1991 | Hauck et al. |
| (Continued) | | |

FOREIGN PATENT DOCUMENTS

| EP | 1102198 | 5/2001 |
|---|---|---|
| WO | WO2008027297 | 3/2008 |

OTHER PUBLICATIONS

Riedel, "Diagnosing pulmonary embolism." Postgrad Med J 2004;80:309-319.*

(Continued)

*Primary Examiner* — Navin Natnithithadha
*Assistant Examiner* — Eric Messersmith
(74) *Attorney, Agent, or Firm* — Faegre Baker Daniels LLP

(57) ABSTRACT

Systems and methods provide for ambulatorily sensing pulmonary artery pressure from within a patient, and producing a pulmonary artery pressure measurement from the sensed pulmonary artery pressure. Power is ambulatorily provided within the patient to facilitate sensing of the pulmonary artery pressure and producing of the pulmonary artery pressure measurement. Acute pulmonary embolism is detected based on a change or rate of change in the pulmonary artery pressure measurement. An alert is preferably generated in response to detecting pulmonary embolism.

20 Claims, 16 Drawing Sheets

(56) References Cited

U.S. PATENT DOCUMENTS

| | | | |
|---|---|---|---|
| 5,053,008 | A | 10/1991 | Bajaj |
| 5,133,353 | A | 7/1992 | Hauser |
| 5,179,945 | A | 1/1993 | Van Hofwegen et al. |
| 5,284,136 | A | 2/1994 | Hauck et al. |
| 5,313,953 | A | 5/1994 | Yomtov et al. |
| 5,314,459 | A | 5/1994 | Swanson et al. |
| 5,318,597 | A | 6/1994 | Hauck et al. |
| 5,334,222 | A | 8/1994 | Salo et al. |
| 5,376,106 | A | 12/1994 | Stahmann et al. |
| 5,388,578 | A | 2/1995 | Yomtov et al. |
| 5,411,031 | A | 5/1995 | Yomtov |
| 5,540,727 | A | 7/1996 | Tockman et al. |
| 5,620,466 | A | 4/1997 | Haefner et al. |
| 5,662,688 | A | 9/1997 | Haefner et al. |
| 5,836,987 | A | 11/1998 | Baumann et al. |
| 6,026,320 | A | 2/2000 | Carlson et al. |
| 6,044,298 | A | 3/2000 | Salo et al. |
| 6,055,454 | A | 4/2000 | Heemels |
| 6,221,011 | B1 | 4/2001 | Bardy |
| 6,270,457 | B1 | 8/2001 | Bardy |
| 6,277,072 | B1 | 8/2001 | Bardy |
| 6,277,078 | B1 | 8/2001 | Porat et al. |
| 6,280,380 | B1 | 8/2001 | Bardy |
| 6,285,907 | B1 | 9/2001 | Kramer et al. |
| 6,336,903 | B1 | 1/2002 | Bardy |
| 6,358,203 | B2 | 3/2002 | Bardy |
| 6,368,284 | B1 | 4/2002 | Bardy |
| 6,371,922 | B1 | 4/2002 | Baumann et al. |
| 6,398,728 | B1 | 6/2002 | Bardy |
| 6,411,848 | B2 | 6/2002 | Kramer et al. |
| 6,424,865 | B1 | 7/2002 | Ding |
| 6,440,066 | B1 | 8/2002 | Bardy |
| 6,459,929 | B1 | 10/2002 | Hopper et al. |
| 6,542,775 | B2 | 4/2003 | Ding et al. |
| 6,597,951 | B2 | 7/2003 | Kramer et al. |
| 6,666,826 | B2 | 12/2003 | Salo et al. |
| 6,764,446 | B2 | 7/2004 | Wolinsky |
| 6,840,956 | B1 | 1/2005 | Wolinsky |
| 6,892,095 | B2 | 5/2005 | Salo |
| 7,186,220 | B2 | 3/2007 | Stahmann et al. |
| 7,198,603 | B2 | 4/2007 | Penner |
| 7,207,945 | B2 | 4/2007 | Bardy |
| 7,273,457 | B2 | 9/2007 | Penner |
| 7,283,874 | B2 | 10/2007 | Penner |
| 7,442,169 | B2 | 10/2008 | O Rourke |
| 7,445,601 | B2 | 11/2008 | Kline |
| 7,480,528 | B2 | 1/2009 | Brockway et al. |
| 7,566,308 | B2 | 7/2009 | Stahmann |
| 7,572,228 | B2 | 8/2009 | Wolinsky |
| 7,575,553 | B2 | 8/2009 | Stahmann et al. |
| 7,610,094 | B2 | 10/2009 | Stahmann et al. |
| 7,641,619 | B2 | 1/2010 | Penner |
| 7,662,101 | B2 | 2/2010 | Lee et al. |
| 7,998,084 | B2 | 8/2011 | Kline |
| 2004/0172083 | A1 | 9/2004 | Penner |
| 2004/0215089 | A1* | 10/2004 | Bergelson ............ A61B 5/0006 600/510 |
| 2004/0260374 | A1 | 12/2004 | Zhang |
| 2005/0159666 | A1 | 7/2005 | Pearce et al. |
| 2006/0047205 | A1* | 3/2006 | Ludomirsky et al. ........ 600/486 |
| 2006/0064133 | A1* | 3/2006 | Von Arx et al. ............... 607/17 |
| 2006/0094967 | A1* | 5/2006 | Bennett et al. ............... 600/508 |
| 2006/0116590 | A1 | 6/2006 | Fayram |
| 2006/0155200 | A1 | 7/2006 | Ng |
| 2006/0167358 | A1* | 7/2006 | Karamanoglu ...... A61B 5/0215 600/485 |
| 2007/0088221 | A1* | 4/2007 | Stahmann ..................... 600/485 |
| 2007/0129637 | A1 | 6/2007 | Wolinsky |
| 2007/0129646 | A1 | 6/2007 | Heinonen et al. |
| 2007/0274565 | A1 | 11/2007 | Penner |
| 2008/0234535 | A1 | 9/2008 | Malak et al. |
| 2009/0088651 | A1 | 4/2009 | Shuros |

OTHER PUBLICATIONS

Rodger et al., "Diagnostic value of the electrocardiogram in suspected pulmonary embolism." The American Journal of Cardiology, Oct. 1, 2000;86:807-809.*

Van de Werf, et al. "Management of acute myocardial infarction in patients presenting with ST-segment elevation." European Heart Journal (2003) 24, 28-66.*

Goldhaber SZ, et al. Acute pulmonary embolism: clinical outcomes in the International Cooperative Pulmonary Embolism Registry (ICOPER). Lancet 1999;353:1386-9.

Linblad B, et al. Incidence of venous thromboembolism verified by necropsy over 30 years. Br Med J 1991;302:709-11.

Nakayama Y, et al. Characteristics of Pulmonary Artery Pressure Waveform for Differential Diagnosis of Chronic Pulmonary Thromboembolism and Primary Pulmonary Hypertension. J Am Coll Cardiol 1997;29:1311-6.

Yoshinaga T, et al. Serial changes in negative T wave on electrocardiogram in acute pulmonary thromboembolism. Int J Cardiol 1999;72:65-72.

McGinn S, et al. Acute cor pulmonale resulting from pulmonary embolism. J Am Med Assoc 1935;104:1473-80.

Pulmonary Embolism, Physician's Desk Reference, printed from internet Mar. 27, 2009 http://www.pdrhealth.com/patient_education/BHG01CA10.shtml.

DVTs and all that [Apr. 2003; 110-2], Arch Intern Med. Mar. 23, 1998;158(6):585-93.

Ignatescu et al., Plasma Lp(a) levels are increased in patients with chronic thromboembolic pulmonary hypertension, Thrombosis and Haemostasis, vol. 80, No. 2, Aug. 1998, pp. 231-232.

Stobo et al., "Unstable Angina and Acute Myocardial Infarction", The Principles and Practice of Medicine, Ch. 13, Prentice Hall, Jun. 24, 1996, pp. 16-27.

Weinberger, Principles of Pulmonary Medicine, Ch. 13-14, 2003.

Written Opinion from counterpart PCT Application, App. No. PCT/US2009/038826, dated Jul. 7, 2009.

File history for U.S. Appl. No. 12/414,465.

* cited by examiner

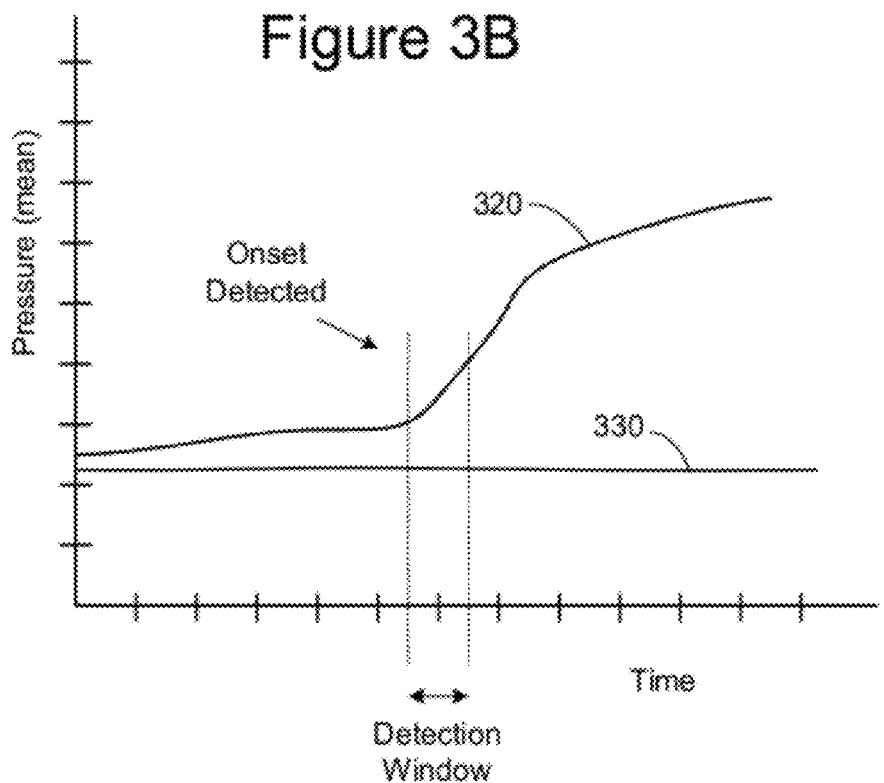
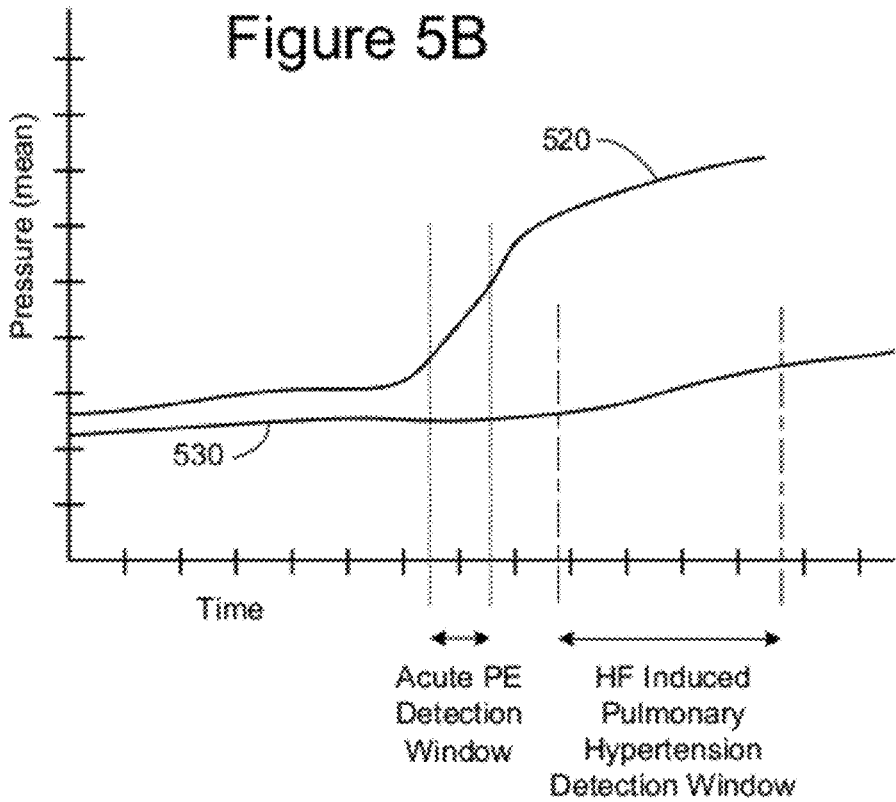

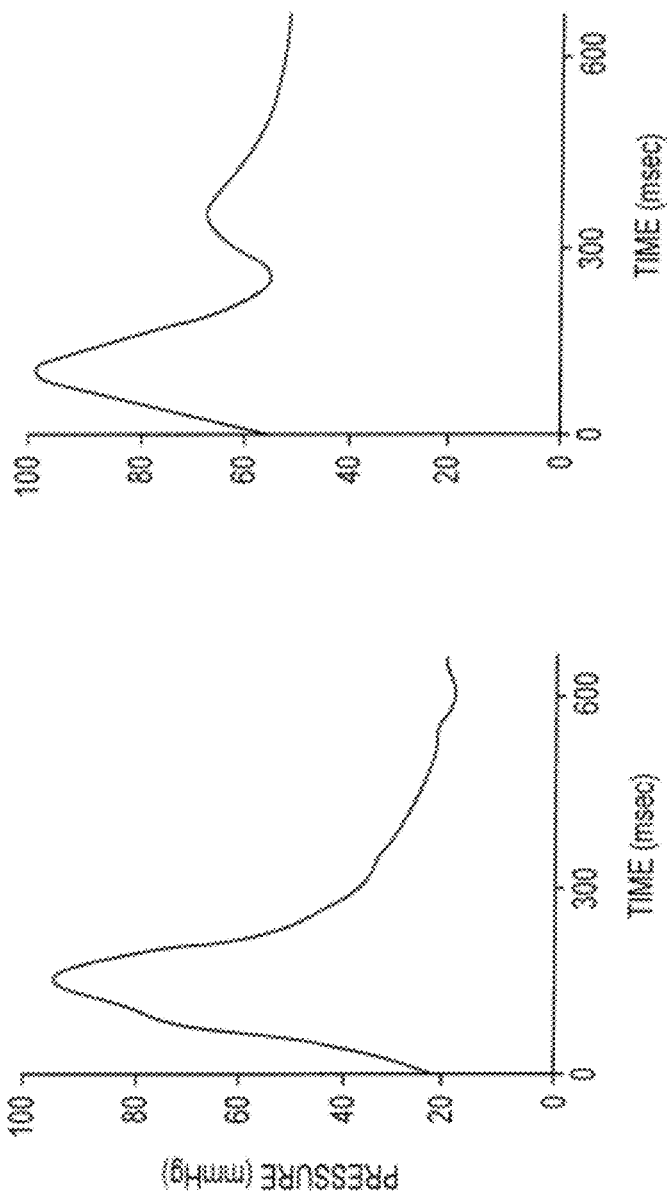

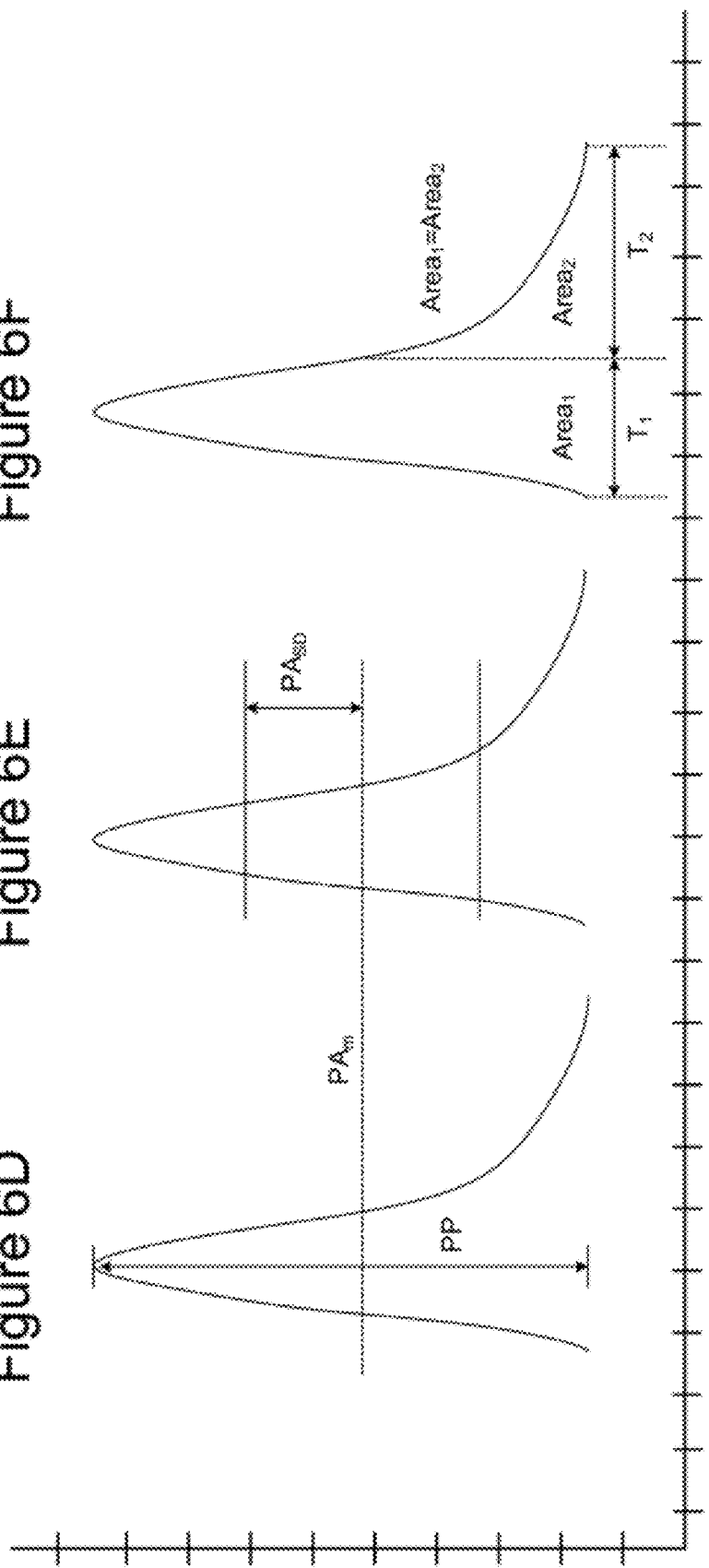

Figure 8A
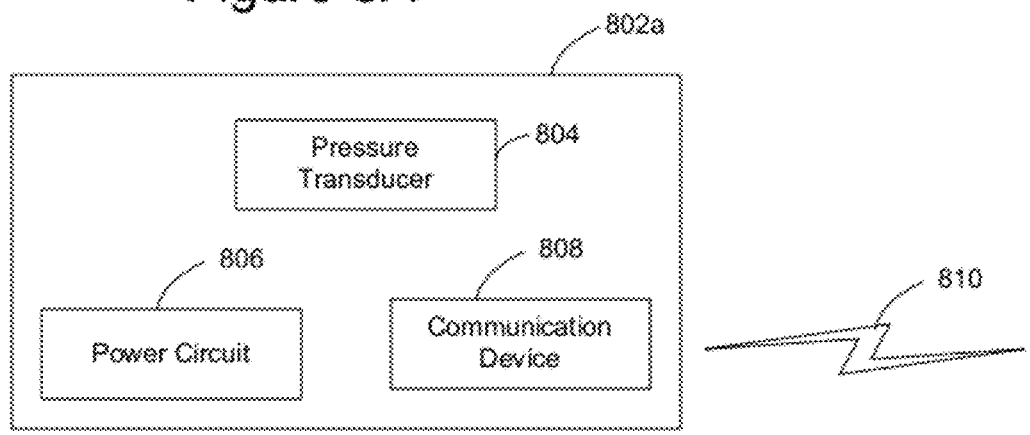
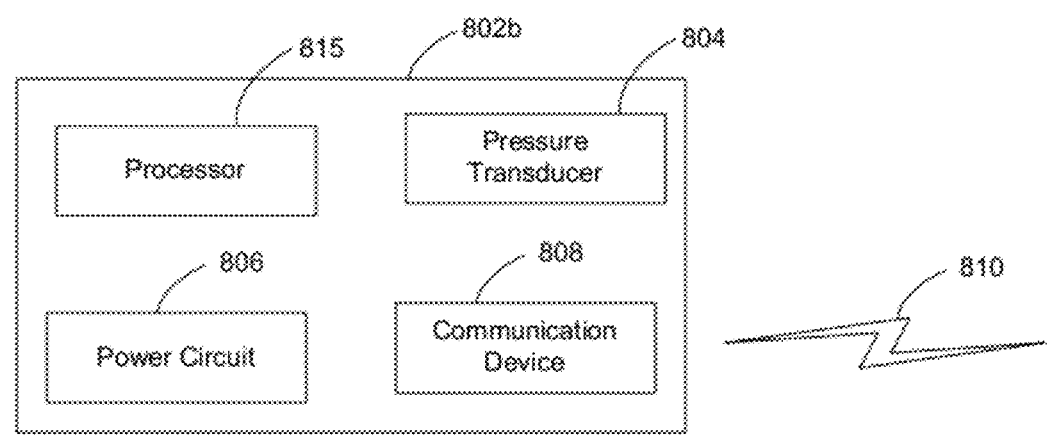
Figure 8B

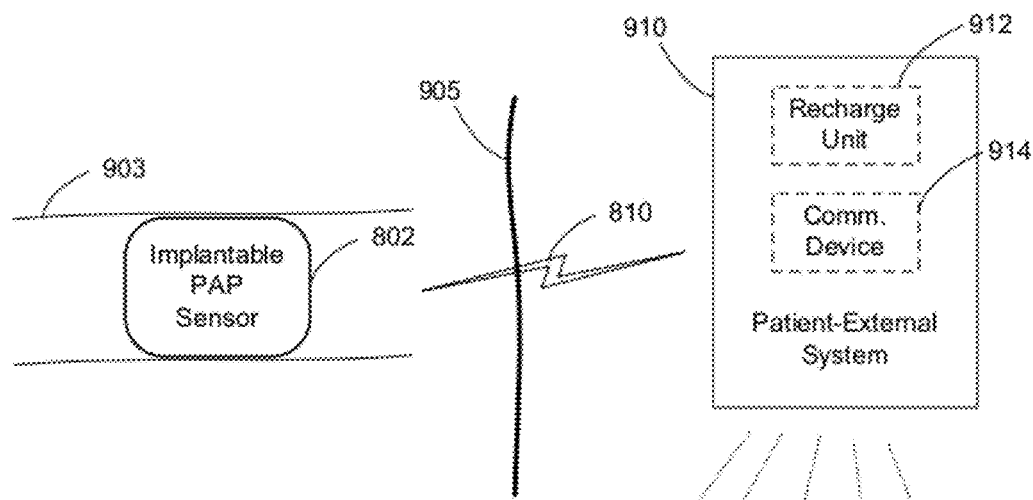
Figure 9
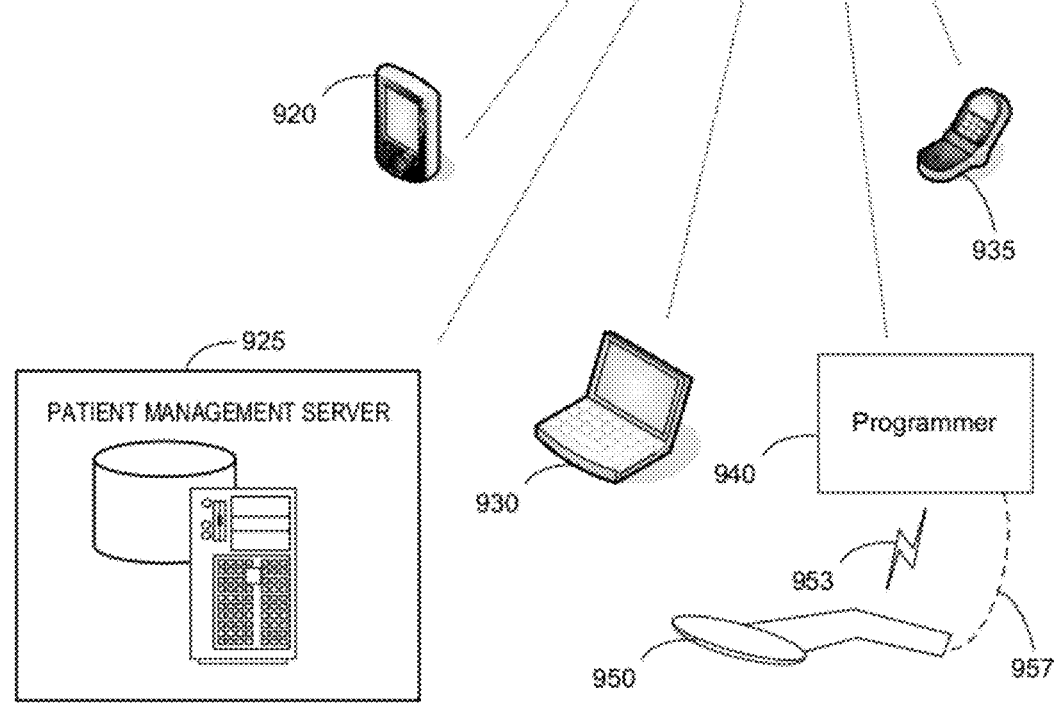

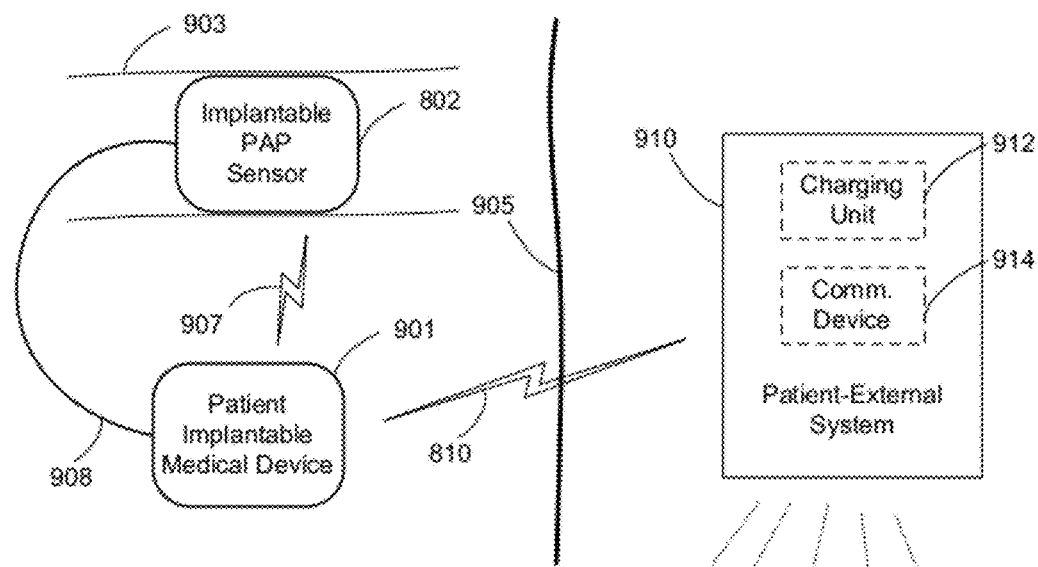
Figure 10
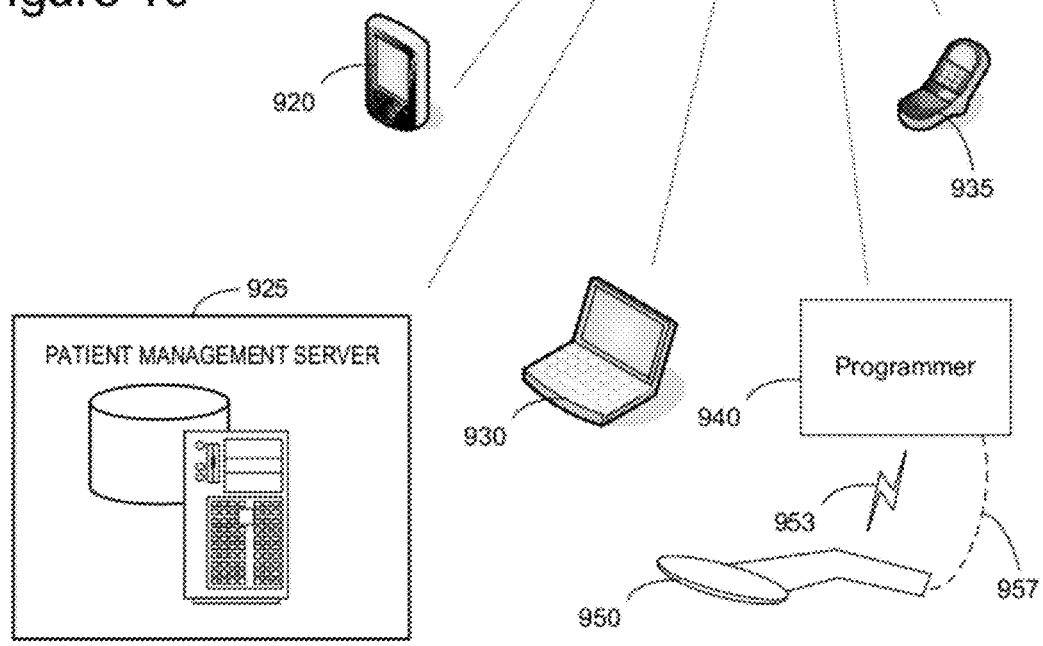

SYSTEM AND METHOD FOR DETECTION OF PULMONARY EMBOLISM

RELATED APPLICATIONS

This application is a continuation of U.S. patent application Ser. No. 12/414,465, filed on Mar. 30, 2009, to issue as U.S. Pat. No. 8,147,415 on Apr. 3, 2012, and claims the benefit of Provisional Patent Application Ser. No. 61/126,860, filed May 7, 2008, to which priority is claimed pursuant to 35 USC §120 and 35 USC §119(e), respectively, and both of which are hereby incorporated herein by reference.

FIELD OF THE INVENTION

The present invention relates generally to detection of pulmonary disorders, and more particularly, to systems and methods for detecting pulmonary embolism and for distinguishing acute pulmonary embolism from other pulmonary and cardiac disorders.

BACKGROUND OF THE INVENTION

Pulmonary embolism is a common disorder accompanied by a significant morbidity and mortality. Thromboembolism may either be acute through activation of the blood clotting system and disseminated intravascular coagulation, or occur at a later stage through the formation of thrombi in the pulmonary vessels or formation in the venous circulation with subsequent embolisation to the lung. The mortality rate for patients with pulmonary embolism is higher than in patients with acute myocardial infarction, exceeding 10% at 30 days and 16% at 3 months according to various studies. It has been estimated that pulmonary embolism accounts for 10% of all deaths in hospitals, and is a major contributing factor in a further 10%.

Pregnant women, and in particular women undergoing caesarean section, cancer patients, trauma victims, and patients undergoing surgery (e.g., orthopaedic surgery) are at risk. Further risk groups include individuals confined to bed rest or other types of confinement or restriction in the movement of the body of limbs, both during medical treatment or recovery from such treatment, or during transportation, (e.g., travel by air). Further risk groups include patients with infections and those suffering from diseases or undergoing pharmaceutical treatments that can disturb the blood clotting system or the system for resolution of blood clots.

Deep venous thrombosis (DVT) with the attendant risk of pulmonary embolism and post phlebitic syndrome is a frequent complication in older patients who have undergone surgery, suffered trauma or who have serious illness such as malignancy or sepsis. In any category, patients who are 40 years of age or older are considered to be at greatest risk. Also, the longer the period of immobilization the greater the risk of DVT. Other factors that have been reported to contribute to development of DVT are obesity, prior history of DVT, and smoking. Heart failure patients have increased risk of DVT on the order of three times that of the general population.

SUMMARY OF THE INVENTION

The present invention is directed to systems and methods for detection of pulmonary disorders including pulmonary embolism and pulmonary hypertension. Systems and methods of the present invention are also directed to discriminating between different etiologies of pulmonary embolism and pulmonary hypertension, and between pulmonary embolism and myocardial infarction. Systems and methods of the present invention are further directed to detection of acute pulmonary embolism using pulmonary artery pressure measurements and verifying presence of acute pulmonary embolism using cardiac electrical signals.

Methods according to embodiments of the present invention involve ambulatorily sensing pulmonary artery pressure from within a patient, and producing a pulmonary artery pressure measurement from the sensed pulmonary artery pressure. Power is ambulatorily provided within the patient to facilitate the sensing of the pulmonary artery pressure and the producing of the pulmonary artery pressure measurement. Acute pulmonary embolism is detected based on a change in the pulmonary artery pressure measurement. An alert is preferably generated in response to detecting pulmonary embolism.

Systems according to embodiments of the present invention include an implantable pressure sensor configured to ambulatorily sense pulmonary artery pressure from within a patient. The pressure sensor preferably includes a support structure comprising a stabilizing arrangement configured to stabilize the pressure sensor within a pulmonary artery of the patient, a pressure transducer, and a communications device coupled to the pressure transducer. The communications device is configured to effect wireless or wired transmission of a pulmonary artery pressure waveform out of the patient's pulmonary artery. The pressure transducer and the communications device are supported by the support structure. A battery is configured to supply power for the pressure transducer and the communications device. A processor is communicatively coupled to the communications device of the pressure sensor. The processor is configured to execute programmed instructions for detecting acute pulmonary embolism based on a change in a pulmonary artery pressure measurement derived from the pulmonary artery pressure waveform.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 3B is a graph that illustrates morphological differences between pulmonary artery pressure waveforms associated with acute pulmonary embolism and primary pulmonary hypertension that can be detected for purposes of discriminating between acute pulmonary embolism and primary pulmonary hypertension in accordance with embodiments of the invention;

FIG. 5B is a graph that illustrates morphological differences between pulmonary artery pressure waveforms associated with acute pulmonary embolism and heart failure induced pulmonary hypertension that can be detected for purposes of discriminating between acute pulmonary embolism and heart failure induced pulmonary hypertension in accordance with embodiments of the invention;

FIGS. 6B and 6C show pulmonary artery pressure waveforms indicative of chronic pulmonary hypertension and primary pulmonary hypertension, respectively, morphological differences of which may be used to discriminate between chronic pulmonary embolism and primary pulmonary hypertension in accordance with embodiments of the invention;

FIGS. 6D-6F illustrate features of a pulmonary artery pressure waveform that can be used to develop indexes useful for discriminating between chronic pulmonary embolism and primary pulmonary hypertension in accordance with embodiments of the invention;

FIG. 8A is a block diagram showing an ambulatory pulmonary artery pressure sensor in accordance with embodiments of the invention;

FIG. 8B is a block diagram showing an ambulatory pulmonary artery pressure sensor in accordance with embodiments of the invention;

FIG. 9 is a block diagram showing a system that includes an ambulatory pulmonary artery pressure sensor that may be implemented to detect pulmonary disorders and discriminate between different etiologies of pulmonary disorders and cardiac disorders in accordance with embodiments of the invention; and FIG. 10 is a block diagram showing a system that includes an ambulatory pulmonary artery pressure sensor and a patient-implantable medical device that may be implemented to detect pulmonary disorders and discriminate between different etiologies of pulmonary disorders and cardiac disorders in accordance with embodiments of the invention.

Figure 1A:
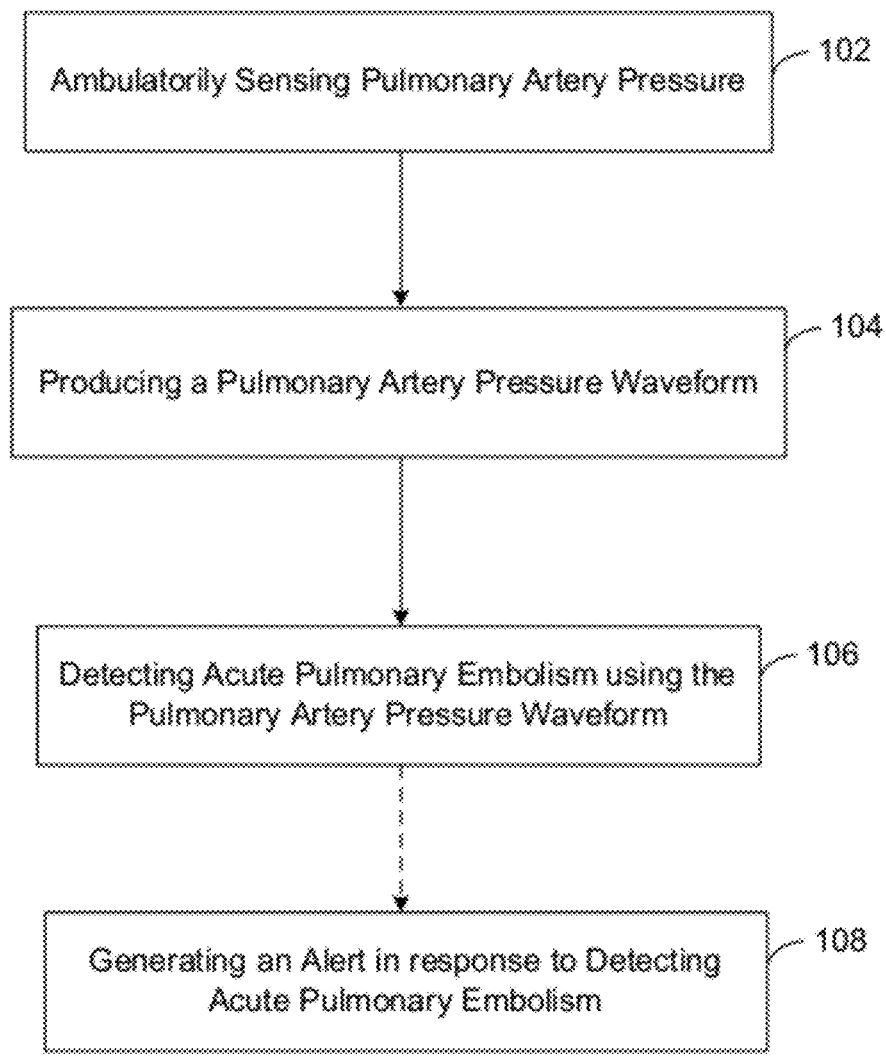
FIG. 1A is a flow diagram illustrating detection of acute pulmonary embolism using ambulatorily sensed pulmonary artery pressure in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device, system or method may be implemented to include one or more of the advantageous features and/or processes described below. It is intended that such device, system or method need not include all of the features described herein, but may be implemented to include selected features that provide for useful structures and/or functionality. Such a device, system or method may be implemented to provide a variety of diagnostic and/or therapeutic functions.

According to embodiments of the present invention, an implantable pulmonary artery pressure sensor is configured for ambulatory sensing of a patient's pulmonary artery pressure. Intracardiac pulmonary artery pressure indicates not only a patient's heart condition, but also pulmonary function and respiration condition, since pulmonary artery pressure is modulated by intrathoracic pressure, which is directly related to lung function.

A pulmonary artery pressure sensor of the present invention preferably incorporates, or is otherwise coupled to, a communications device that is capable of transmitting pulmonary artery pressure sensor information out of the pulmonary artery. A processor is configured to execute programmed instructions for detecting one or more pulmonary disorders, and may also be configured to discriminate between various etiologies of pulmonary and cardiac disorders.

In some embodiments, a patient-external system is employed to receive sensor information transmitted from the pulmonary artery pressure sensor. The patient-external system may include, for example, a programmer, a computing device or system such as a PC, or a hand-held health care provider manipulatible device or reader. The patient-external system may be configured with a communications device that facilitates communication between a server system and the patient-external system. Communication between the pulmonary artery pressure sensor and patient-external system may be unidirectional or bidirectional.

In system configurations that incorporate a server system, such as an advanced patient management system, communication among the pulmonary artery pressure sensor, patient-external system, and server system may be any combination of unidirectional or bidirectional modalities. The processor that executes programmed instructions for detecting pulmonary disorders and discriminating between various etiologies of pulmonary and cardiac disorders may be incorporated in, or distributed among, the pulmonary artery pressure sensor, the patient-external system, and the server system.

In other embodiments, a body implantable device, such as a patient-implantable medical device, is configured with a communications device to effect communication with the pulmonary artery pressure sensor. The communication link between the patient-implantable medical device and the pulmonary artery pressure sensor may be unidirectional or bidirectional. The patient-implantable medical device incorporates a communications device that facilitates communication between the patient-implantable medical device and a patient-external system, which may further communicate with a server system. Communication among the pulmonary artery pressure sensor, patient-external system, and server system may be any combination of unidirectional or bidirectional modalities. The processor that executes programmed instructions for detecting pulmonary disorders and discriminating between various etiologies of pulmonary and cardiac disorders may be incorporated in, or distributed among, the pulmonary artery pressure sensor, the patient-implantable medical device, the patient-external system, and the server system.

A wide variety of patient-implantable medical devices may be configured to communicate with a pulmonary artery pressure sensor and a patient-external system in accordance with embodiments of the present invention. A non-limiting, representative list of such devices includes a relatively simple monitoring device that includes a communications device and memory, a nerve stimulation device, a drug delivery device, and a cardiac monitoring device. More sophisticated devices include pacemakers, cardiovertors, defibrillators, resynchronizers, and other cardiac sensing and therapy delivery devices. These devices may be configured with a variety of electrode arrangements, including surface, transvenous, endocardial, and epicardial electrodes (i.e., intrathoracic electrodes), and/or subcutaneous, non-intrathoracic electrodes, and subcutaneous array or lead electrodes (i.e., non-intrathoracic electrodes). Such devices are referred to herein generally as a patient-implantable medical device (PIMD) for convenience, it being understood that such a medical device may alternatively be implemented at least in part as a patient-external medical device.

Turning now to FIG. 1A, there is shown a flow diagram illustrating detection of acute pulmonary embolism using ambulatorily sensed pulmonary artery pressure in accordance with embodiments of the invention. The implementation shown in FIG. 1A involves ambulatorily sensing pulmonary artery pressure from within a patient 102, and producing 104 a pulmonary artery pressure waveform indicative of the sensed pulmonary artery pressure. Acute pulmonary embolism is detected 106 using the pulmonary artery pressure waveform. Acute pulmonary embolism may be detected based on a change in a feature of the pulmonary artery pressure waveform, such as a change measurable relative to a threshold. For example, detecting acute pulmonary embolism may involve detecting a change in a morphological feature of the pressure waveform relative to a baseline of the morphological feature established for the patient.

The threshold may define a baseline pulmonary artery pressure value determined for the patient, such as a pulmonary artery pressure value (e.g., an averaged value) measured for the patient prior to onset of acute pulmonary embolism. Such a baseline may define a pulmonary artery pressure value for a patient that is at high risk of acute pulmonary embolism but presently does not evidence an acute or non-acute etiology of pulmonary embolism or pulmonary hypertension. Such a baseline may define a pulmonary artery pressure value for a patient that is at high risk of acute pulmonary embolism and presently evidences a non-acute etiology of pulmonary embolism or pulmonary hypertension, such as chronic pulmonary embolism (also referred to as chronic pulmonary thromboembolism), primary pulmonary embolism, or heart failure induced pulmonary hypertension.

A patient's baseline pulmonary artery pressure value may alternatively be established based at least in part on relevant patient population data. The relevant patient population data from which a patient's baseline pulmonary artery pressure value may be established is typically dependent on whether or not a patient presently evidences a non-acute etiology of pulmonary embolism or pulmonary hypertension, and if so, what form of pulmonary embolism or pulmonary hypertension is present. A patient's baseline pulmonary artery pressure value may also be established based on a blending of patient-specific pulmonary artery pressure information and patient population data.

The threshold may also define a metric that indicates the degree of change or rate of change in the feature of the pulmonary artery pressure waveform. Suitable metrics include a preestablished percent change or rate of change of the waveform feature over a specified time duration (e.g., detection window). The threshold may be defined based on other metrics, such as standard deviation or coefficient of variation of the pulmonary artery pressure waveform feature. Suitable metrics that may be developed from a variety of detectable waveform features include the absolute value or peak of the pulmonary artery pressure waveform, the slope or trending of the slope of the pulmonary artery pressure waveform, width of the pulmonary artery pressure waveform, fractional pulse pressure of the pulmonary artery pressure waveform, average or mean value of the pulmonary artery pressure waveform, coefficient of variation or other metric involving the standard deviation, total or partial area under the pulmonary artery pressure waveform, and timing aspects of these features. The threshold may be defined by a multiplicity of such features and/or metrics, and may involve a multiplicity of timing or detection windows associated with such features and/or metrics. The detection algorithms may use different thresholds for different patient statuses such as indicated by other sensors' inputs. An example of the input could be an accelerometer-based activity sensor.

In some embodiments, acute pulmonary embolism is detected from within the patient. For example, a pulmonary artery pressure waveform produced ambulatorily within a patient's pulmonary artery may be communicated wirelessly from a location at which the pulmonary artery pressure is sensed to a second location within the patient. The pulmonary artery pressure waveform may be communicated through a lead from the location at which the pulmonary artery pressure is sensed to a second location within the patient.

Detecting acute pulmonary embolism may be performed at the second location. In other embodiments, acute pulmonary embolism is detected externally from the patient. By way of example, a pulmonary artery pressure waveform produced ambulatorily within a patient's pulmonary artery may be wirelessly communicated from a location at which the pulmonary artery pressure is sensed or other patient-internal location to a second location externally of the patient. Detecting acute pulmonary embolism may be performed at the second location.

The methodology shown in FIG. 1A is primarily directed to acute pulmonary embolism detection. However, it is considered desirable to generate 108 an alert in response to detecting acute pulmonary embolism. The alert may be communicated to one or more of the patient, a health care advocate of the patient, and the patient's health care provider. The alert may take a variety of forms including an audible tone or alert message, a visual alert, or a signal that can be communicated to one or more of the patient, a health care advocate of the patient, and a patient's health care provider (e.g. physician or nurse) and subsequently converted to audible tone/message and/or a visual alert (e.g., textual, graphical, and/or sensor information). The alert is preferably of a type that draws immediate attention to the patient's acute pulmonary embolism condition, and indicates the seriousness of this condition.

The alert may be communicated via a patient-external system or device and/or via a patient management server system. In embodiments that include a patient-implantable medical device, it may be desirable for the PIMD to generate an alert, such as by broadcasting an audible alert tone that can be heard by the patient or health care advocate or by transmitting an alert signal to a patient-external system and/or patient management server system.

Figure 1B:
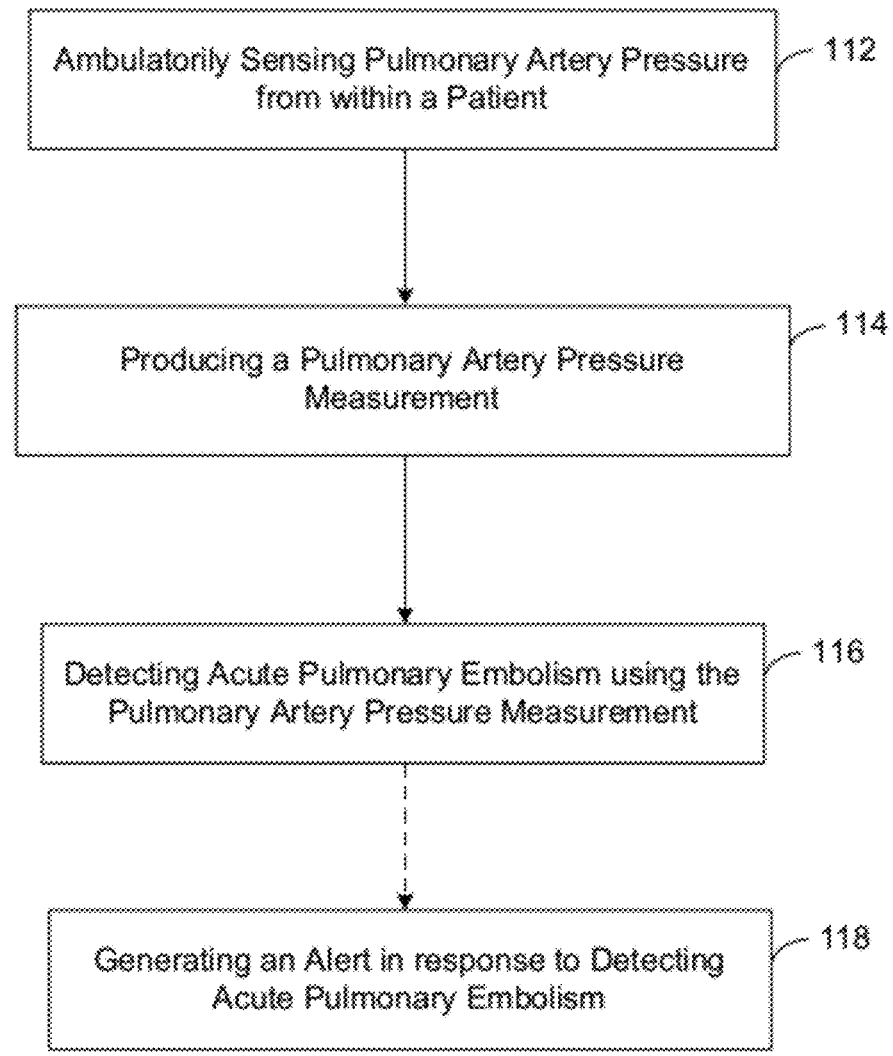
FIG. 1B is a flow diagram illustrating detection of acute pulmonary embolism using ambulatorily sensed pulmonary artery pressure in accordance with embodiments of the invention.

FIG. 1B is a flow diagram illustrating detection of acute pulmonary embolism using ambulatorily sensed pulmonary artery pressure. The implementation in FIG. 1B involves ambulatorily sensing 112 pulmonary artery pressure from within a patient, producing 114 a pulmonary artery pressure measurement from the sensed pulmonary artery pressure, and detecting 116 acute pulmonary embolism using the pulmonary artery pressure measurement. Acute pulmonary embolism may be detected based on a change in a feature of the pulmonary artery pressure measurement, such as a change in diastolic or systolic pressure relative to a threshold as discussed herein. As in the embodiment shown in FIG. 1A, it is considered desirable to generate 118 an alert in response to detecting acute pulmonary embolism. The alert is preferably communicated to one or more of the patient, a health care advocate of the patient, and the patient's health care provider.

Figure 1C:
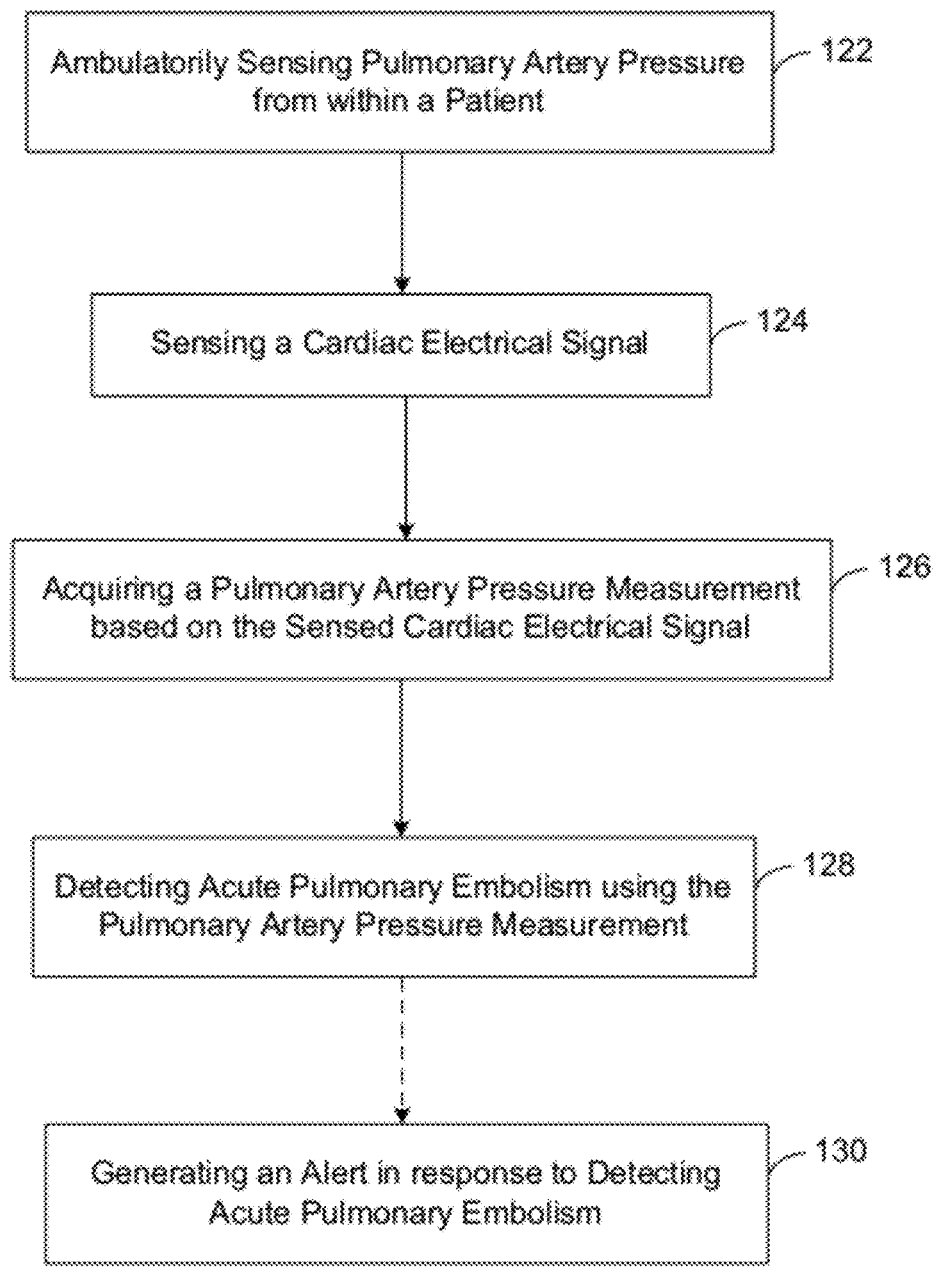
FIG. 1C is a flow diagram illustrating detection of acute pulmonary embolism using ambulatorily sensed pulmonary artery pressure in accordance with embodiments of the invention.

FIG. 1C is a flow diagram illustrating detection of acute pulmonary embolism using ambulatorily sensed pulmonary artery pressure. FIG. 1C involves ambulatorily sensing 122 pulmonary artery pressure from within a patient, and sensing 124 a cardiac electrical signal, which may be performed within the patient or patient-externally. Cardiac electrical signals are analyzed by a processing system to detect phases (e.g., systole and diastole) and/or events (e.g., end of systole, end of diastole) within the cardiac cycle such as systole and diastole. The cardiac phases or events are used to determine when in the cardiac cycle to acquire 126 a pulmonary artery pressure measurement. Energy may be saved and unneeded pulmonary artery pressure samples can be avoided by sampling the pulmonary artery pressure waveform only at time(s) of interest. FIG. 1C further involves detecting 128 acute pulmonary embolism using the pulmonary artery pressure measurement. As in the embodiment shown in FIGS. 1A and 1B, it is considered desirable to generate 130 an alert in response to detecting acute pulmonary embolism. The alert is preferably communicated to one or more of the patient, a health care advocate of the patient, and the patient's health care provider.

Figure 2A:
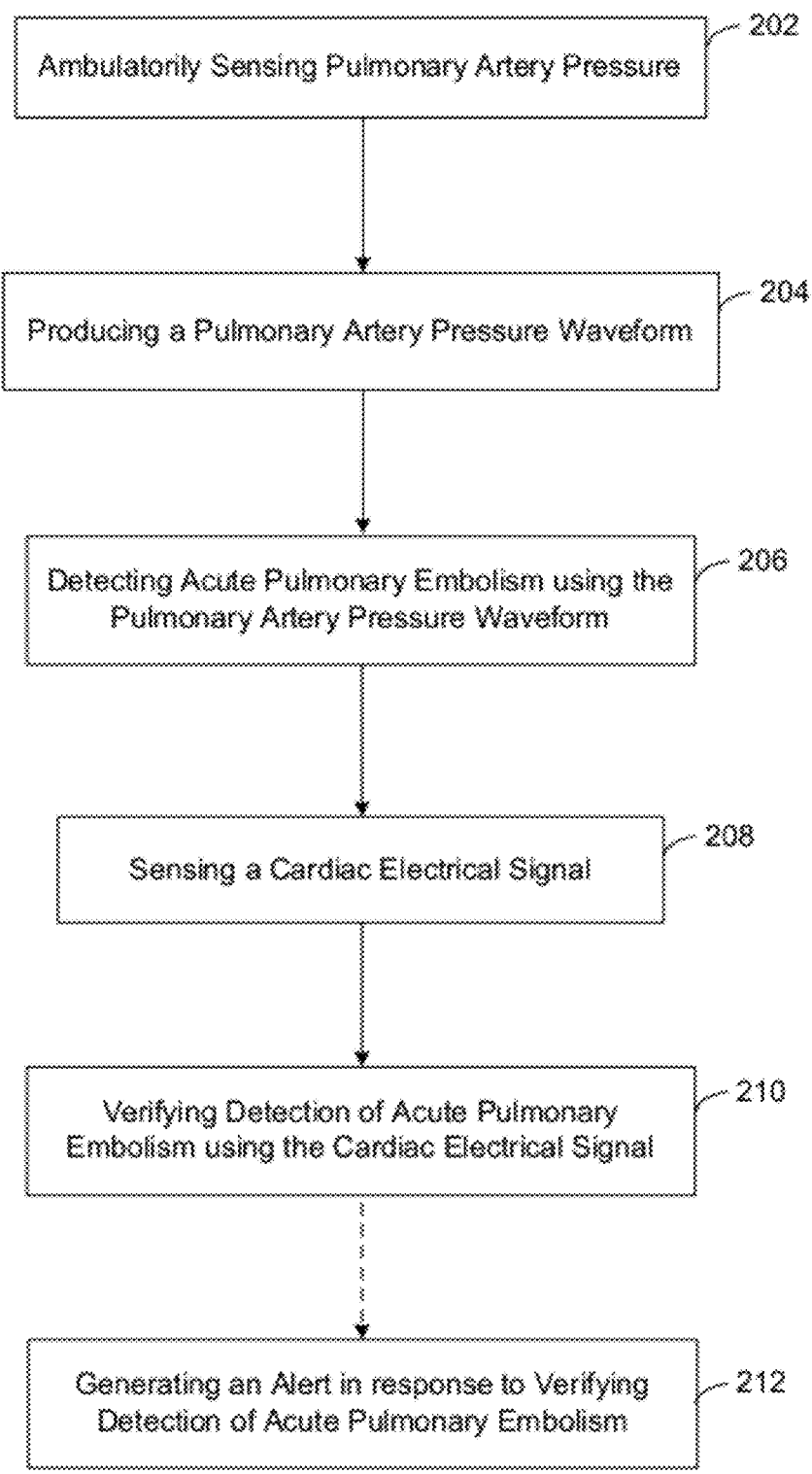
FIG. 2A is a flow diagram illustrating detection of acute pulmonary embolism using ambulatorily sensed pulmonary artery pressure and verification of the detected acute pulmonary embolism using a cardiac electrical signal in accordance with embodiments of the invention.

FIG. 2A is a flow diagram illustrating detection of acute pulmonary embolism using ambulatorily sensed pulmonary artery pressure and verification of the detected acute pulmonary embolism using a cardiac electrical signal in accordance with embodiments of the invention. The implementation shown in FIG. 2A involves ambulatorily sensing pulmonary artery pressure from within a patient 202, producing 204 a pulmonary artery pressure waveform indicative of the sensed pulmonary artery pressure, and detecting 206 acute pulmonary embolism using the pulmonary artery pressure waveform. Acute pulmonary embolism may be detected based on a change in a feature of the pulmonary artery pressure waveform, such as a change in a morphological feature of the pressure waveform measurable relative to a threshold as discussed above.

The methodology illustrated in FIG. 2A further involves sensing 208 a cardiac electrical signal, which may be performed within the patient or patient-externally. The cardiac electrical signals are analyzed by a processing system to verify 210 presence of acute pulmonary embolism as detected by analysis of the pulmonary artery pressure information. As in the embodiment shown in FIG. 1, it is considered desirable to generate 212 an alert in response to detecting acute pulmonary embolism. The alert is preferably communicated to one or more of the patient, a health care advocate of the patient, and the patient's health care provider.

In some embodiments, an implantable cardiac monitoring or stimulation device (e.g., PIMD) may sense electrograms or electrocardiograms (ECG). The cardiac electrical signals acquired by the PIMD may be analyzed by the processor of the PIMD or a processor of a patient-external system to verify presence of acute pulmonary embolism as detected by analysis of the pressure information acquired by the pulmonary artery pressure sensor.

In other embodiments, a patient-external surface ECG recorder (e.g., a 12-lead ECG recorder) may be used to acquire cardiac signals that can be analyzed by the recorder, PC, or other patient-external processing system to verify presence of acute pulmonary embolism as detected by analysis of the pressure information acquired by the pulmonary artery pressure sensor. In one configuration, the patient-external surface ECG recorder is configured to wirelessly transmit cardiac electrical signals to the processor that also analyzes the pulmonary artery pressure information, and this processor may be incorporated in a patient management server system or a processor-based system local to the patient.

Figure 2B:
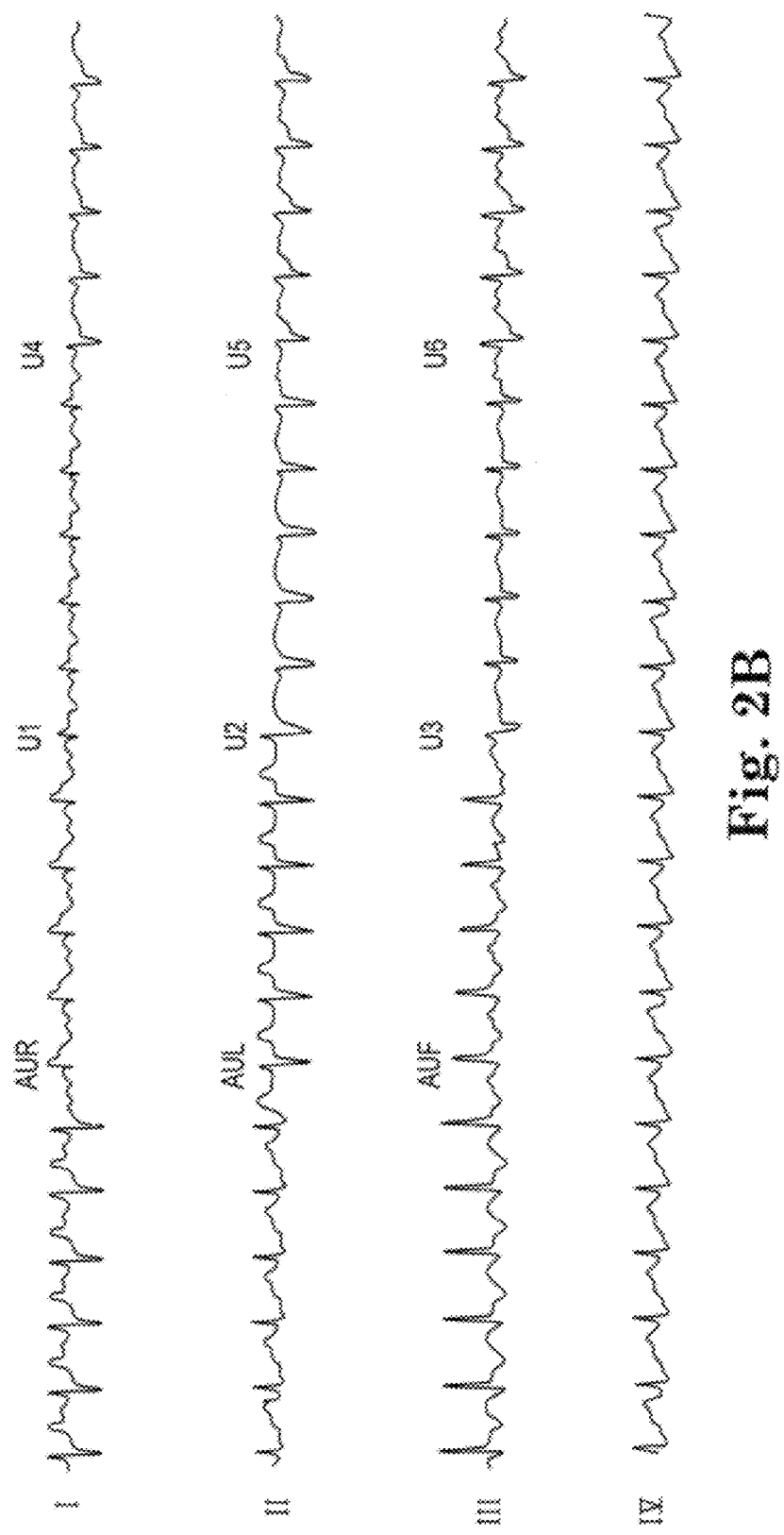
FIG. 2B are cardiac electrical signal waveforms that show an S1Q3T3 pattern that indicates presence of acute pulmonary embolism.

FIG. 2B shows cardiac electrical waveforms acquired by use of a 12-lead ECG recorder for a patient that has acute pulmonary embolism. The S1Q3T3 pattern shown in FIG. 2B has been reported in a large number of patients having acute pulmonary embolism. In the ECG graph shown in FIG. 2B, Lead I had a large S-wave, Lead III has a large Q-wave and inverted T-wave. This characteristic pattern may be used to confirm detection of acute pulmonary embolism detected by use of ambulatorily sensed pulmonary artery pressure information.

In one approach, a template may be produced from patient population data that is indicative of an S1Q3T3 pattern or other pattern that indicates presence of acute pulmonary embolism. Various known template matching methodologies may be used, such as those involving correlational techniques (e.g., feature correlation coefficient techniques) or pattern recognition, among others. According to a semi-manual approach, an algorithm may be employed that identifies presence of an S1Q3T3 pattern in the ECG waveforms and adds marker channel data to a waveform display or printout, thus allowing the health care provider to readily confirm presence of acute pulmonary embolism as detected by analysis of ambulatorily sensed pulmonary artery pressure information acquired implantably from the patient. Other approaches may be used to confirm presence of acute pulmonary embolism, such as use of MRI, X-ray, CT or other imaging technique, for example.

Figure 3A:
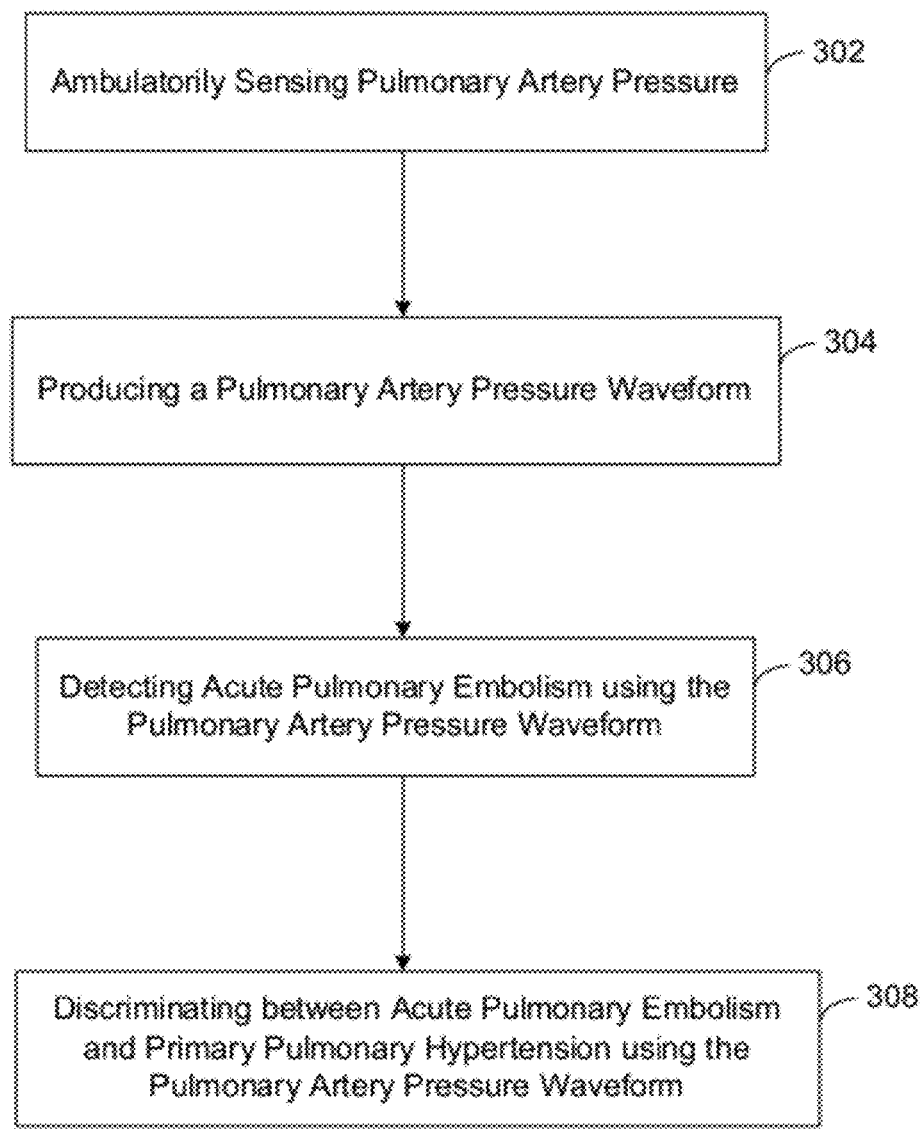
FIG. 3A is a flow diagram illustrating detection of acute pulmonary embolism using ambulatorily sensed pulmonary artery pressure and discriminating between acute pulmonary embolism and primary pulmonary hypertension in accordance with embodiments of the invention.

FIG. 3A is a flow diagram illustrating detection of acute pulmonary embolism using ambulatorily sensed pulmonary artery pressure and discriminating between acute pulmonary embolism and primary pulmonary hypertension in accordance with embodiments of the invention. The implementation shown in FIG. 3A involves ambulatorily sensing pulmonary artery pressure from within a patient 302, producing 304 a pulmonary artery pressure waveform indicative of the sensed pulmonary artery pressure, and detecting 306 acute pulmonary embolism using the pulmonary artery pressure waveform, such as in a manner previously discussed. The methodology of FIG. 3A further involves discriminating 308 between acute pulmonary embolism and primary pulmonary hypertension using the pulmonary artery pressure waveform.

According to various embodiments, acute pulmonary embolism may be distinguished from primary pulmonary hypertension based on detection of an appreciable change of the pulmonary artery pressure signal morphology within a relatively short period of time. FIG. 3B shows a pulmonary artery pressure signal 330 for a patient that has primary pulmonary hypertension and a pulmonary artery pressure signal 320 for a patient that experiences acute pulmonary embolism. As can be seen in FIG. 3B, the amplitude of the pulmonary artery pressure signal 330 for the patient having primary pulmonary hypertension remains relatively constant or increases relatively slowly (e.g., a slow rate of change of signal 330) over an extended time period (e.g., days, weeks, years).

In contrast, it can be seen that the amplitude of the pulmonary artery pressure signal 320 for the patient that experiences acute pulmonary embolism increases significantly over a relatively short time period (e.g., minutes, hours). Onset of acute pulmonary embolism may be detected by detecting an increase in the amplitude of the pulmonary artery pressure signal 320 (or increased rate of change of signal 320) during detection windows having a length defined in minutes or hours.

Figure 4:
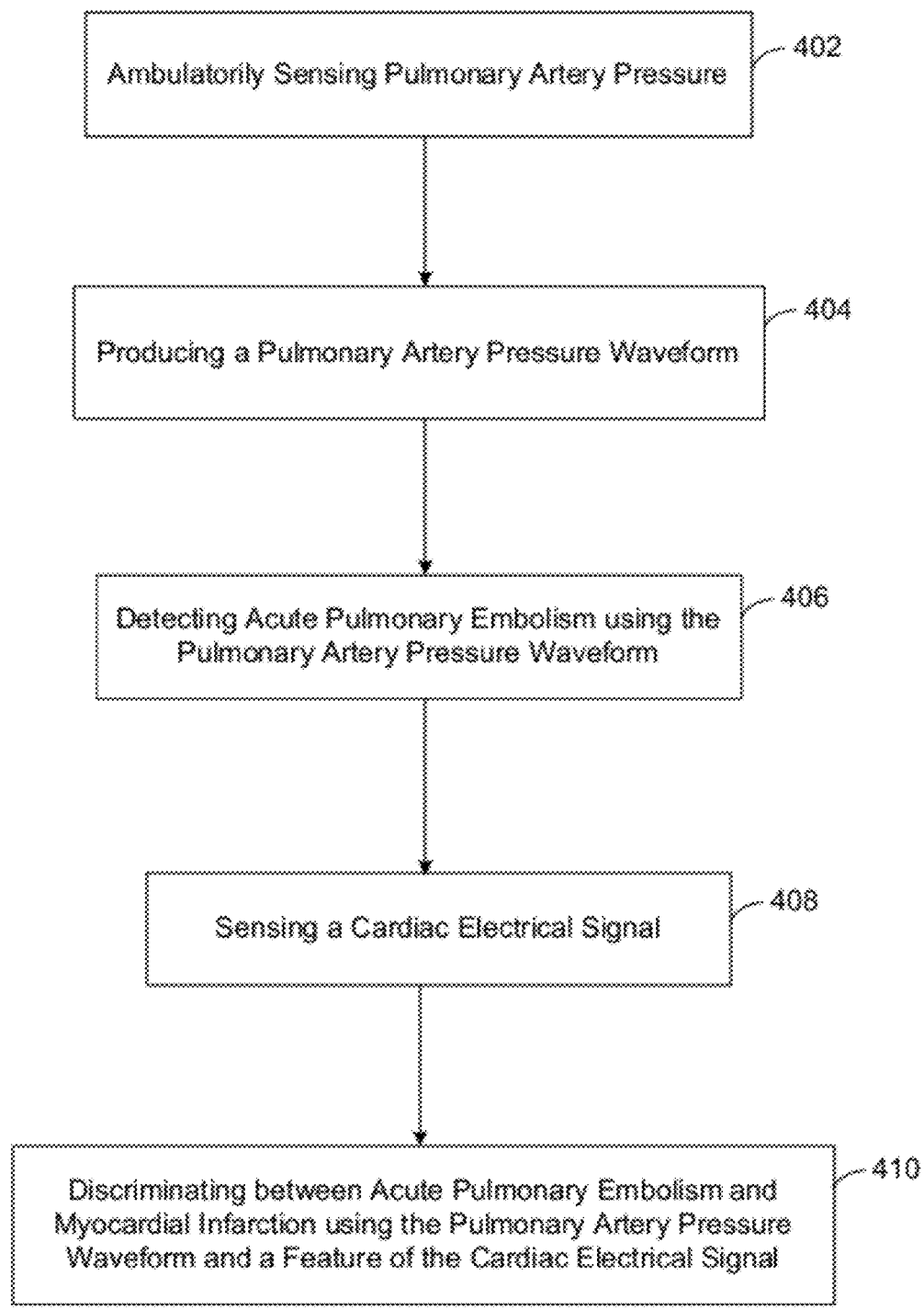
FIG. 4 is a flow diagram illustrating detection of acute pulmonary embolism using ambulatorily sensed pulmonary artery pressure and discriminating between acute pulmonary embolism and myocardial infarction in accordance with embodiments of the invention.

FIG. 4 is a flow diagram illustrating detection of acute pulmonary embolism using ambulatorily sensed pulmonary artery pressure and discriminating between acute pulmonary embolism and myocardial infarction (MI) in accordance with embodiments of the invention. Discriminating between acute pulmonary embolism and MI has traditionally been difficult, since these conditions have common symptoms such as chest pains and shortness of breath.

The implementation shown in FIG. 4 involves ambulatorily sensing pulmonary artery pressure from within a patient 402, producing 404 a pulmonary artery pressure waveform indicative of the sensed pulmonary artery pressure, and detecting 406 acute pulmonary embolism using the pulmonary artery pressure waveform, such as in a manner previously discussed. The methodology of FIG. 4 further involves sensing a cardiac electrical signal 408 and discriminating 410 between acute pulmonary embolism and MI using the pulmonary artery pressure waveform and a feature of the cardiac electrical signal. The cardiac electrical signal may be acquired in a manner discussed previously.

According to various embodiments, acute pulmonary embolism may be distinguished from MI based on detection of an appreciable change in the ST segment, T wave or Q wave of the patient's cardiac electrical. During MI (and assuming absence of acute pulmonary embolism onset), an elevation or depression in the ST segment, T wave inversion and/or a "significant" Q wave (e.g., an initial downward deflection of the Q wave of about 40 ms or more in any lead except III and aVR) may occur. Conversely, in the absence of MI and assuming the patient experiences onset of acute pulmonary embolism, the ST segment and Q wave may either be absent of ECG abnormalities or have different ST and Q wave patterns from the MI pattern, such as a gradual staircase ascent of the ST interval from S to T wave in lead 2. It is understood that MI can often be detected by changes in a patient's ST segment and/or Q wave. The effects on the ECG due to an MI are complex but generally depend on the type and severity of the MI. A transmural MI will commonly result in acute ST segment elevation, T-wave inversion and a significant Q wave. A subendocardial MI will commonly result in ST segment depression and T wave inversion without evidence of significant Q waves. Acute ischemia not associated with an MI also typically acutely affects the ECG. Commonly during acute ischemia the ECG will show ST segment depression, ST segment elevation, and/or symmetrically inverted T waves. The effects of the ischemia are temporary and the ECG returns to normal when adequate blood flow returns to the myocardium.

Figure 5A:
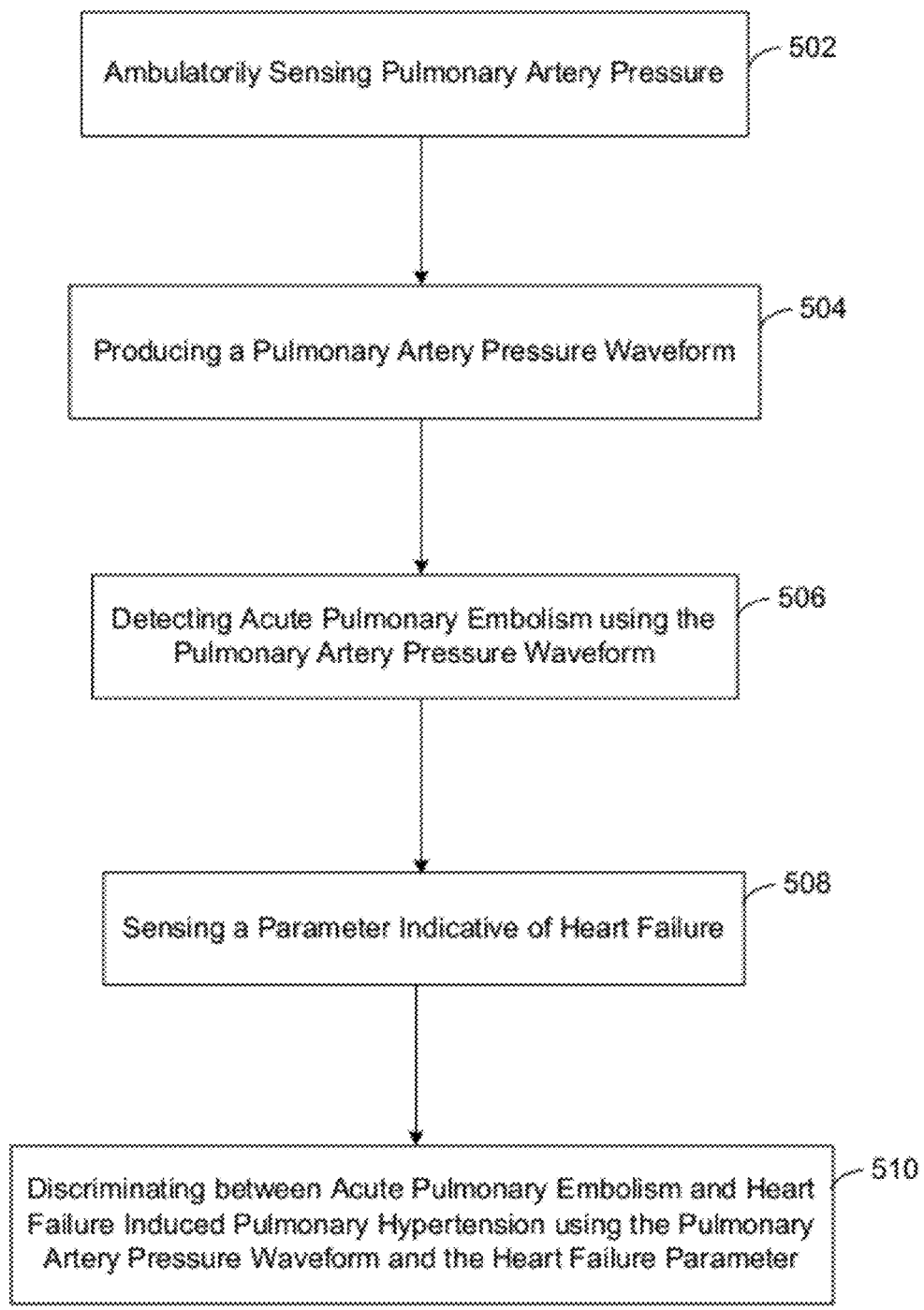
FIG. 5A is a flow diagram illustrating detection of acute pulmonary embolism using ambulatorily sensed pulmonary artery pressure and discriminating between acute pulmonary embolism and heart failure induced pulmonary hypertension in accordance with embodiments of the invention.

FIG. 5A is a flow diagram illustrating detection of acute pulmonary embolism using ambulatorily sensed pulmonary artery pressure and discriminating between acute pulmonary embolism and heart failure induced pulmonary hypertension in accordance with embodiments of the invention. The implementation shown in FIG. 5A involves ambulatorily sensing pulmonary artery pressure from within a patient 502, producing 504 a pulmonary artery pressure waveform indicative of the sensed pulmonary artery pressure, and detecting 506 acute pulmonary embolism using the pulmonary artery pressure waveform, such as in a manner previously discussed. The methodology of FIG. 5 further involves sensing 508 a parameter indicative of heart failure and discriminating 510 between acute pulmonary embolism and hear failure induced pulmonary hypertension using the pulmonary artery pressure waveform and the heart failure parameter.

Various parameters indicative of a patient's heart failure status may be sensed within the patient or patient-externally. For example, one or more sensors may be configured to monitor certain physiological parameters indicative of a patient's heart failure status (e.g., thoracic fluid via thoracic impedance or other sensor, heart sounds, respiration, heart rate, heart rate variability, electrogram conduction pattern, blood chemistry, blood pressure, potassium levels, blood perfusion, blood oxygen saturation, body or limb temperature, patient weight). Various system embodiments may include those that incorporate one or more implantable sensors, one or more patient-external sensor, or a combination of internal and patient-external sensors.

According to embodiments directed to implantable devices, a PIMD may incorporate or be coupled to one or more implantable sensors. One or more of the sensors are configured to sense a physiologic parameter or condition indicative of the patient's heart failure status. Such sensors may include one or more of a thoracic impedance sensor (e.g., implanted transthoracic total impedance sensor), a blood (internal filling) pressure sensor, blood flow sensor, blood perfusion sensor (e.g., plethysmography sensor), blood temperature sensor, blood gas sensor (e.g., oximeter sensor), heart sounds sensor (e.g., accelerometer or microphone), and blood chemistry or composition sensor (e.g., $PO_2$ sensor, $SAO_2$ sensor, glucose sensor, potassium sensor, lactate sensor, $PCO_2$ sensor, pH sensor, and molecular probe). Examples of suitable blood (internal filling) pressure sensors, blood flow sensors, blood temperature sensors, and associated detection techniques are described in commonly-owned U.S. Pat. Nos. 6,666,826 and 6,892,095, which are hereby incorporated herein by reference.

A variety of external sensors may also be used to sense various physiological parameters that are useful for determining a patient's heart failure status. Such external sensors may include one or more of a pulse oximetry sensor, blood pressure sensor, blood chemistry sensor, patient temperature sensor, patient weight sensor, and ECG sensor arrangement, among others.

FIG. 5B is a graph that illustrates morphological differences between pulmonary artery pressure waveforms associated with acute pulmonary embolism and heart failure (HF) induced pulmonary hypertension that can be detected for purposes of discriminating between acute pulmonary embolism and heart failure induced pulmonary hypertension in accordance with embodiments of the invention. FIG. 5B shows a pulmonary artery pressure signal 530 for a patient that has HF induced pulmonary hypertension and a pulmonary artery pressure signal 520 for a patient that experiences acute pulmonary embolism. As can be seen in FIG. 5B, the amplitude of the pulmonary artery pressure signal 530 for the patient having HF induced pulmonary hypertension increases relatively slowly (e.g., rate of change of the signal 530) over an extended time period (e.g., days, such as 1-7 days, and more particularly 1-3 days).

In contrast, it can be seen that the amplitude of the pulmonary artery pressure signal 520 for the patient that experiences acute pulmonary embolism increases significantly over a relatively short time period, as is discussed above with reference to FIG. 3B. Onset of acute pulmonary embolism may be detected by detecting an increase in the amplitude (or increased rate of change) of the pulmonary artery pressure signal 520 during a detection window having a length defined in minutes or hours (e.g., 15 minutes). Heart failure induced pulmonary hypertension may be detected by detecting a change in the diastolic pulmonary artery pressure signal 530 amplitude in the range of 18 to 30 mmHg within a detection window of between about 1-7 days in length. Alternatively or additionally, HF induced pulmonary hypertension may be detected by an increase in the diastolic pulmonary artery pressure of about 20 to 40% within a detection window of between about 1-7 days.

Figure 6A:
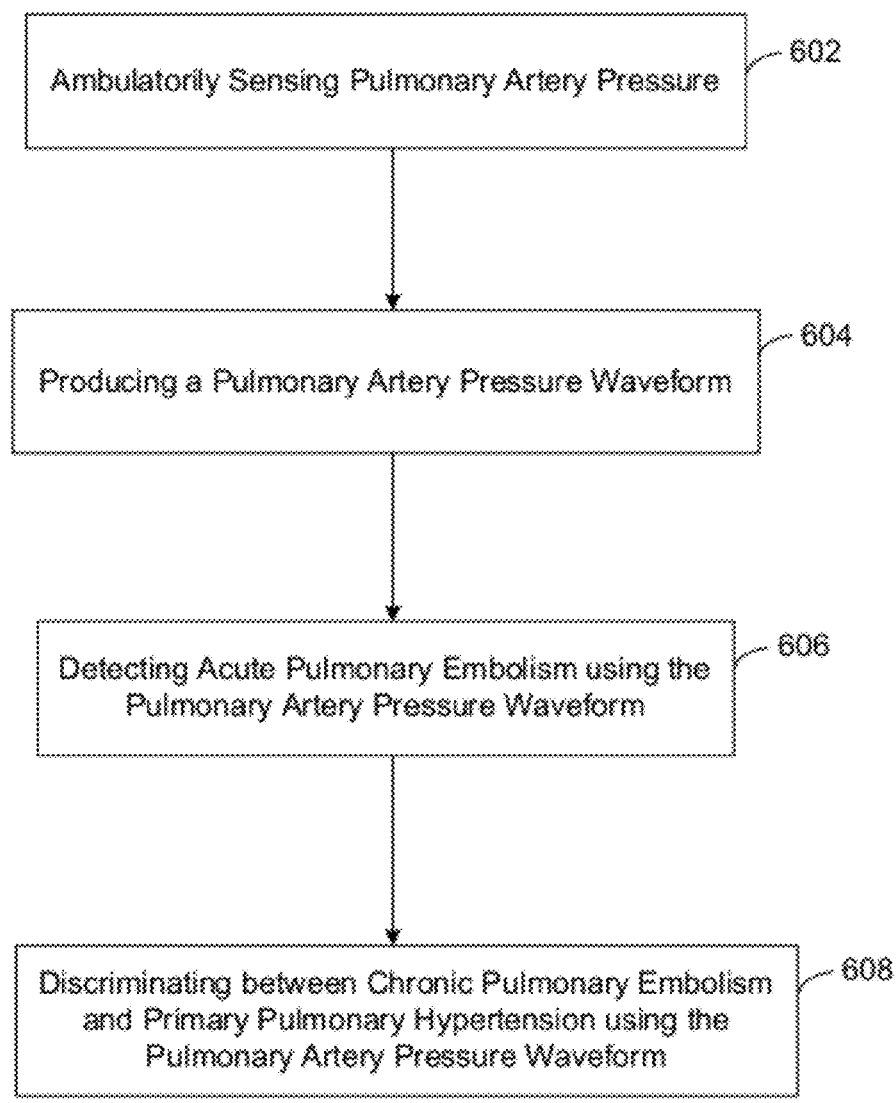
FIG. 6A is a flow diagram illustrating detection of acute pulmonary embolism using ambulatorily sensed pulmonary artery pressure and discriminating between chronic pulmonary embolism and primary pulmonary hypertension in accordance with embodiments of the invention.

FIG. 6A is a flow diagram illustrating detection of acute pulmonary embolism using ambulatorily sensed pulmonary artery pressure and discriminating between chronic pulmonary embolism and primary pulmonary hypertension in accordance with embodiments of the invention. Discriminating between chronic pulmonary embolism and primary pulmonary hypertension is particularly useful for the health care provider in making the correct diagnosis and selection of possible surgical procedures.

The implementation shown in FIG. 6A involves ambulatorily sensing pulmonary artery pressure from within a patient 602, producing 604 a pulmonary artery pressure waveform indicative of the sensed pulmonary artery pressure, and detecting 606 acute pulmonary embolism using the pulmonary artery pressure waveform, such as in a manner previously discussed. The methodology of FIG. 6A further involves discriminating 608 between chronic pulmonary embolism and primary pulmonary hypertension using the pulmonary artery pressure waveform.

FIGS. 6B and 6C show pulmonary artery pressure waveforms indicative of chronic pulmonary embolism and primary pulmonary hypertension, respectively. Morphological differences of these waveforms may be used to discriminate between chronic pulmonary embolism and primary pulmonary hypertension. It has been shown that the morphology of chronic pulmonary embolism is quite different from that of primary pulmonary hypertension. Chronic pulmonary embolism predominately involves the proximal arteries, whereas primary pulmonary hypertension primarily involves the peripheral arteries.

It is hypothesized that patient's with chronic pulmonary embolism have relatively stiff or high resistance proximal arteries, whereas those with primary pulmonary hypertension have relatively stiff or high resistance peripheral arteries. These differences in the primary lesions results in arterial pulsatility relative to mean pressure larger in the case of chronic pulmonary embolism than in the case of primary pulmonary hypertension. This difference in mean pulmonary artery pressure is shown in FIGS. 6B and 6C. It can also be seen that the morphology or overall shape of the two waveforms are significantly different.

In one embodiment, primary pulmonary hypertension is distinguished from chronic pulmonary embolism by measurement of the diastolic and systolic pulmonary pressures. If the patient's diastolic pulmonary artery pressure is greater than, for example, a range of 15 to 30 mmHg, and a systolic pulmonary artery pressure patient is greater than, for example, a range of 35 to 50 mmHG, the patient would have primary pulmonary hypertension. If patient's diastolic pulmonary artery pressure is less than, for example, a range of 15 to 30 mmHg, and a systolic pulmonary artery pressure patient is greater than, for example, a range of 35 to 50 mmHG, the patient would have chronic pulmonary embolism. In another embodiment, if the patient's pulmonary artery pressure monotonically decreases from the systolic peak to the nadir of the diastolic pressure in presence of systolic pulmonary hypertension, then the patient would have chronic pulmonary embolism. Alternately, if the patient's pulmonary artery pressure has two significant peaks within a cardiac cycle and the patient has one or more of systolic (e.g., above a range of 35 to 50 mmHg) and diastolic pulmonary hypertension (e.g., above a range of 15 to 30 mmHG), then the patient would have primary pulmonary hypertension.

FIGS. 6D-6F illustrate features of a pulmonary artery pressure waveform that can be used to develop indexes useful for discriminating between chronic pulmonary embolism and primary pulmonary hypertension in accordance with embodiments of the invention. To quantify the accentuated pulsatility in the pulmonary artery pressure waveform, three indexes may be computed and used to discriminate between chronic pulmonary embolism and primary pulmonary hypertension.

Referring to FIG. 6D, fractional pulmonary artery pulse pressure ($PP_f$) may be defined as:

$$PP_f = \frac{PP}{PA_m}$$

where PP is the pulse pressure and $PA_m$ is the mean pulmonary artery pressure. Referring to FIG. 6E, coefficient of variation (CV) may be defined as:

$$CV = \frac{PA_{SD}}{PA_m}$$

where $PA_{SD}$ is the standard deviation of pulmonary artery pressure. Referring to FIG. 6F, factional time to halve the area ($TA_{1/2}$) may be defined as:

$$TA_{1/2} = \frac{T_1}{T_1 + T_2}$$

where $T_1$ is defined as the time at which the area under the pressure curve over the $T_1$ period ($Area_1$) equals the rest of the area ($Area_2$).

According to the above results, criteria for differentiating chronic pulmonary embolism (CPE) and primary pulmonary hypertension (PPH) may be as follows:

If $PP_f$ is greater than 1.1, then CPE, otherwise PPH;
If CV is greater than 0.35, then CPE, otherwise PPH;
If $TA_{1/2}$ is less than 0.385, then CPE, otherwise PPH.

Detection performance can be further improved using the following weighted index:

$$PAP_i = 0.4*PP_f + 0.4*CV + 0.2*TA_{1/2}$$

If $PAP_i$ is less than ⅔, then CPE, otherwise PPH.

Figure 7:
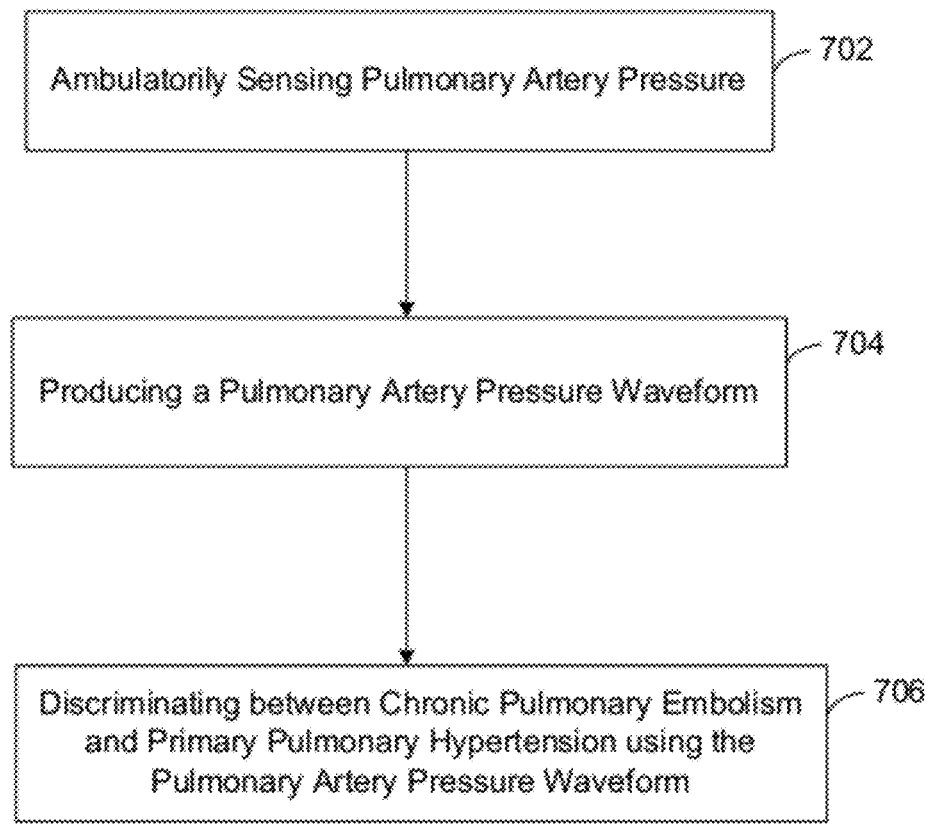
FIG. 7 is a flow diagram illustrating a methodology for discriminating between chronic pulmonary embolism and primary pulmonary hypertension in accordance with embodiments of the invention.

FIG. 7 is a flow diagram illustrating a methodology for discriminating between chronic pulmonary embolism and primary pulmonary hypertension in accordance with embodiments of the invention. This embodiment is similar to that shown in FIG. 6A, except for the absence of detecting acute pulmonary embolism. The implementation shown in FIG. 7 involves ambulatorily sensing pulmonary artery pressure from within a patient 702, producing 704 a pulmonary artery pressure waveform indicative of the sensed pulmonary artery pressure, and discriminating 706 between chronic pulmonary embolism and primary pulmonary hypertension using the pulmonary artery pressure waveform, which may be performed using the methodologies discussed above.

FIG. 8A is a block diagram showing an ambulatory pulmonary artery pressure sensor in accordance with embodiments of the invention. The pressure sensor 802a is preferably configured for chronic implantation within the pulmonary artery or vasculature proximate the pulmonary artery. The pressure sensor 802a is preferably of a type that can remain chronically implanted within the pulmonary artery or neighboring vasculature for an extended period of time, such as weeks, months or years.

The pressure sensor 802a shown in FIG. 8A includes a pressure transducer 804, a communications device 808, and a power circuit 806. The pressure sensor 802a is configured for implantation within a patient's pulmonary artery or vasculature proximate the pulmonary artery. A power source of the power circuit 806 ambulatorily provides power for pressure sensor circuitry 802a and the communications device 808. The pressure transducer 804 may include an accelerometer, a MEMS sensor, strain gauge, piezoresistive, capacitive, transductive, or other type of pressure transducer.

According to other embodiments, pulmonary artery pressure may be implantably and ambulatorily measured without entering the pulmonary artery. According to one implementation, wall deflections of the pulmonary artery can be measured via a vessel adjacent to the pulmonary artery. The arterial wall deflections can be used to detect systolic blood pulses and measure various parameters of the cardiac output and arterial blood flow. Use of such a sensor measures wall deflections of a vessel adjacent to the pulmonary artery, and as such, a pulmonary artery pressure measurement can be conducted without invasively disturbing the pulmonary artery. A suitable sensor for this application is disclosed in commonly owned U.S. Patent Publication No. 2009/0088651, which is incorporated herein by reference.

The communications device 808 is coupled to the pressure transducer 804, and is configured to effect wireless transmission 810 of a pulmonary artery pressure waveform out of the patient. The communications device 808 may comprise, for example, an ultrasonic, acoustic, inductive, optical or RF communications device. The power circuit 806 may include a battery or other energy source, which may be primary (non-rechargeable), chargeable or rechargeable. For example, the power circuit 806 may include an energy harvesting (EH) device that is excited by body movement, thermal changes, and/or acoustic pressure waves, such as is described in U.S. Pat. Nos. 7,283,874 and 7,283,874, which are incorporated herein by reference. Energy acquired by the EH device is converted to electrical current that is stored in a battery of the power circuit 806.

In other configurations, the power circuit 806 may include an inductive circuit that can be excited by a patient-external source, such as a drive coil or magnet arrangement that radiates a magnetic field. The inductive circuit charges a battery of the power circuit 806 in response to an externally generated magnetic field.

According to one approach, a tank circuit may be implemented in the power circuit 806 that is configured to collect energy from a magnetic field generated by a drive coil or coils of a patient-external recharging unit. The drive coil(s) preferably generate a continuous or discontinuous harmonic magnetic field. The tank circuitry is preferably tuned to resonate at the frequencies that the drive coil(s) are driven. In one illustrative example, the tank circuitry may include two tank circuits set to resonate at different frequencies, such as 90 kHz and 160 kHz, respectively. Each of the resonant tank circuits builds amplitude during a burst produced by the drive coil(s) and then gradually loses signal amplitude after the drive coil(s) is turned off. The time associated with the exponential charging and discharging of the resonant tank circuits is determined by the capacitive and inductive elements in the tank circuits.

One or both of the two coils may be used to generate power for the pressure sensor 802a via an appropriate power regulator or converter circuit (e.g., AC-to-DC converter). In other configurations, one of the coils may be used to generate power while the other is used to transmit pressure sensor data to a patient-external device. Sensor data may be encoded on a waveform that radiates from a transmission circuit driven by the second coil. The data may modulate the waveform and decoded by an envelope detector circuit (e.g., which may include synchronous demodulators) of the patient-external system using known techniques. In this approach, resonant circuitry of the pressure sensor 802a provides for power and communications channels for the sensor 802a.

The pressure transducer 804, communications device 808, and power circuit 806 are supported by a support structure. The support structure comprises a stabilizing arrangement configured to stabilize the pressure sensor 802a within the pulmonary artery. For example, the support structure of the pressure sensor 802*a* may comprise a stent graft configured to radially contract during implantation in a pulmonary artery and expand to stabilize the pressure sensor at an implant site within a pulmonary artery. A suitable stent graft support structure is disclosed in U.S. Pat. No. 6,840,956, which is incorporated herein by reference. Other support structures may be employed, such as hooks on the end of struts contacting the intima of the vessel or a helix placed longitudinally in the vessel and exerting radial force on the intima of the vessel.

FIG. 8B is a block diagram showing an ambulatory pulmonary artery pressure sensor 802*b* in accordance with embodiments of the invention. The pressure sensor 802*b* shown in FIG. 8B is similar to that of FIG. 8A, but further includes a processor 815. The processor 815 is communicatively coupled to the pressure transducer 804 and communications device 808 of the pressure sensor 802*b*. The processor 815 may be configured to execute programmed instructions for detecting acute pulmonary embolism and/or discriminating between various etiologies of pulmonary and cardiac disorders in a manner previously described.

Suitable pressure sensors and approaches for communicating sensor information that may be implemented in accordance with the present invention are disclosed in U.S. Pat. Nos. 6,277,078; 6,764,446; 7,198,603; 7,273,457; 7,198,603; 7,575,228 and 7,641,619 and in U.S. Publication Nos. 2007/0129637 and 2007/0274565, which are incorporated herein by reference.

FIG. 9 is a block diagram showing a system that includes an ambulatory pulmonary artery pressure sensor that may be implemented to detect pulmonary disorders and used to discriminate between different etiologies of pulmonary and cardiac disorders in accordance with embodiments of the invention. The system shown in FIG. 9 includes an implantable pulmonary artery pressure (PAP) sensor 802 shown implanted within a pulmonary artery 903 or vasculature proximate the pulmonary artery. The PAP sensor 802 may be configured in the manner shown in FIG. 8A or 8B. The PAP sensor 802 transmits pressure information via a communications link 810 through the patient's body (via skin surface 905) for reception by a patient-external system 910.

The patient-external system 910 includes a communications device 914 and may optionally include a recharging unit 912. The optional recharging unit 912 may be configured in a manner discussed previously to provide a source for energizing a charging circuit within the PAP sensor 802. The patient-external system 910 may be configured as, or communicate with, a variety of devices, sensors, and systems. For example, the patient-external system 910 may be configured to communicate with various sensors and devices, such as a weight scale (not shown), blood pressure cuff (not shown), pulse oximeter (not shown), or drug delivery device (not shown). The patient-external system 910 may be configured to communicate with a patient management server 925, PDA 920, PC 930, cell phone 935 or a programmer 940.

In other embodiments, the patient-external system 910 may be configured as, or otherwise be incorporated as part of, a PDA 920, PC 930, cell phone 935, or a wired (link 957) or wireless (link 953) hand-held reader 950. Such devices that are configured to ambulatorily receive pulmonary artery pressure information have the advantages of being highly portable and capable of communicating patient information, including PAP sensor information, to a remote location (e.g., patient management server 925) via existing communications infrastructure. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

In some configurations, a wired or wireless hand-held reader 950 may cooperate with a programmer 957 or other system. In other configurations, the hand-held reader 950 may be configured to operate exclusive of a programmer or other system. For example, the hand-held reader 950 may be configured to receive pressure sensor information directly from the PAP sensor 802. The pressure sensor information may be stored in a memory of the hand-held reader 950. Alternatively or in addition, a processor of the hand-held reader 950 may be configured to execute programmed instructions for detecting acute pulmonary embolism and/or discriminating between various etiologies of pulmonary and cardiac disorders in a manner previously described. The hand-held reader 950 may include a user interface with which to interact with the PAP sensor 802 (e.g., interrogate the sensor, perform sensor diagnostics, modify firmware if equipped with a processor or controller) and/or a programmer, server system or other device/system. The user-interface of the hand-held reader 950 may include a display for displaying pressure sensor data and discrimination data, among other information.

FIG. 10 is a block diagram showing a system that includes an ambulatory pulmonary artery pressure sensor and a patient-implantable medical device that may be implemented to detect pulmonary disorders and discriminate between different etiologies of pulmonary disorders in accordance with embodiments of the invention. FIG. 10 is similar to the system shown in FIG. 9, but further incorporates a PIMD 901 that is configured to communicate wirelessly with the PAP sensor 802 via link 907. In other configurations, including those shown in other figures, the PIMD 901 is configured to communicate through a lead 908 with the PAP sensor 802, such as is described in commonly owned U.S. Publication No. 2004/0260374, which is hereby incorporated herein by reference.

The PIMD 901 may include a processor that receives sensor information from the PAP sensor 802 and executes programmed instructions for detecting acute pulmonary embolism and/or discriminating between various etiologies of pulmonary and cardiac disorders in a manner previously described. The PIMD 901 may transmit the pulmonary artery pressure information and/or the detection/discrimination output to the patient-external system 910.

The PIMD 901 may be implemented to communicate with the patient management server 925 or network via the patient-external system 910 or an appropriate communications interface. The PIMD 901 may be used within the structure of an advanced patient management (APM) system. The advanced patient management system allows health care providers to remotely and automatically monitor pulmonary and cardiac functions, as well as other patient conditions. In one example, a PIMD implemented as a monitor, pacemaker, defibrillator, or resynchronization device may be equipped with various telecommunications and information technologies that enable real-time data collection, diagnosis, and treatment of the patient. Other PIMD embodiments described herein may be used in connection with advanced patient management.

By way of example, PIMD 901 may incorporate heart failure features involving dual-chamber or bi-ventricular pacing/therapy, cardiac resynchronization therapy, cardiac function optimization, or other heart failure related methodologies. For example, PIMD 901 may incorporate features of one or more of the following references: commonly owned U.S. Publication No. 2003/0130702 and U.S. Pat. Nos. 6,411,848; 6,285,907; 4,928,688; 6,459,929; 5,334,222; 6,026,320; 6,371,922; 6,597,951; 6,424,865; and 6,542,775, each of which is hereby incorporated herein by reference.

Certain configurations of the PIMD 901 may incorporate various functions traditionally performed by an implantable cardioverter/defibrillator (ICD), and may operate in numerous cardioversion/defibrillation modes as are known in the art. Examples of ICD circuitry, structures and functionality, aspects of which may be incorporated in embodiments of the PIMD 901 are disclosed in commonly owned U.S. Pat. Nos. 5,133,353; 5,179,945; 5,314,459; 5,318,597; 5,620,466; and 5,662,688, which are hereby incorporated herein by reference.

Various configurations of the PIMD 901 may incorporate functions traditionally performed by pacemakers, such as providing various pacing therapies as are known in the art, in addition to, or exclusive of, cardioversion/defibrillation therapies. Examples of pacemaker circuitry, structures and functionality, aspects of which may be incorporated in embodiments of the PIMD 901 are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference.

The PIMD 901 may implement diagnostic and/or monitoring functions as well as, or exclusive of, providing cardiac stimulation therapy. Examples of cardiac monitoring circuitry, structures and functionality, aspects of which may be incorporated in embodiments of the PIMD 901 are disclosed in commonly owned U.S. Pat. Nos. 5,313,953; 5,388,578; and 5,411,031, which are hereby incorporated herein by reference.

The terms "ambulatory" and "ambulatorily" that modify the terms pulmonary artery pressure sensor and sensing pulmonary artery pressure, respectively, are intended to connote implementations in which a pressure sensor is chronically implanted in a patient's pulmonary artery. Provision of a chronically implanted pulmonary artery pressure sensor of the present invention, in contrast to an acute pulmonary artery pressure sensing approach, allows the patient to go about his or her normal routine for extended periods of time, unencumbered by catheters and/or temporary percutaneously sensing apparatuses that are typically used in a hospital setting for conducting short-term invasive clinical evaluations lasting on the order of hours (e.g., 1-10 hours, but <24 hours). In the context of various presently claimed embodiments, a chronically implanted pressure sensor provides for ambulatory sensing of a patient's pulmonary artery pressure for days (e.g., >30 days), weeks, months, or years.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method, comprising:
    ambulatorily sensing pulmonary artery pressure from within a pulmonary artery of a patient;
    ambulatorily sensing, using at least one electrode disposed external to the patient, a first cardiac electrical signal of the patient;
    producing a pulmonary artery pressure measurement from the sensed pulmonary artery pressure and producing a pulmonary artery pressure waveform indicative of the sensed pulmonary artery pressure, wherein timing of the pulmonary artery pressure measurement is based at least in part on the sensed cardiac electrical signal;
    ambulatorily providing power within the patient by at least one of subcutaneously providing power and transcutaneously providing power to facilitate the sensing of the pulmonary artery pressure and the cardiac electrical signal, and the producing of the pulmonary artery pressure measurement;
    detecting acute pulmonary embolism based on a change in a morphological feature of the pulmonary artery pressure waveform;
    ambulatorily sensing, using the at least one electrode, at least one of the first cardiac electrical signal and a second cardiac electrical signal of the patient; and
    verifying detection of the acute pulmonary embolism using the at least one of the first cardiac electrical signal and the second cardiac electrical signal.

2. The method of claim 1, wherein detecting acute pulmonary embolism comprises detecting acute pulmonary embolism based on the change in the morphological feature relative to a threshold, the threshold comprising a baseline of the morphological feature established for the patient.

3. The method of claim 1, wherein detecting acute pulmonary embolism comprises detecting acute pulmonary embolism based on the change in the morphological feature relative to a threshold, the threshold comprising a baseline pulmonary artery pressure value determined for the patient using patient specific data.

4. The method of claim 1, wherein verifying detection of the acute pulmonary embolism includes matching the at least one of the first cardiac electrical signal and the second cardiac electrical signal to a template that is indicative of a pattern that indicates presence of the acute pulmonary embolism.

5. The method of claim 4, wherein the pattern comprises an S1Q3T3 pattern.

6. The method of claim 1, further comprising discriminating between acute pulmonary embolism and myocardial infarction based on a change of the pulmonary artery pressure measurement relative to a change in a feature of the sensed cardiac electrical signal.

7. The method of claim 6, wherein the feature of the sensed cardiac electrical signal comprises an ST segment of the sensed cardiac electrical signal, and discriminating between acute pulmonary embolism and myocardial infarction comprises:
    detecting myocardial infarction as a change in a feature of the ST segment; and
    detecting acute pulmonary embolism as a change in the pulmonary artery pressure measurement in the absence of an appreciable change in the ST segment feature or other myocardial infarction-associated feature of the sensed cardiac electrical signal.

8. The method of claim 1, further comprising discriminating between acute pulmonary embolism and primary pulmonary hypertension based on a rate of change of the pulmonary artery pressure measurement.

9. The method of claim 1, further comprising:
    sensing a parameter indicative of heart failure from within the patient; and discriminating between acute pulmonary embolism and heart failure induced pulmonary hypertension based on a rate of change of the pulmonary artery pressure measurement and a change in the sensed parameter.

10. The method of claim 1, further comprising discriminating between chronic pulmonary embolism and primary pulmonary hypertension based on one or more of a fractional pulse pulmonary artery pressure derived from a waveform indicative of the sensed pulmonary artery pressure, a coefficient of variation of the pulmonary artery pressure derived from the pulmonary artery pressure waveform, and a fractional time to half the area under the pulmonary artery pressure waveform.

11. A system, comprising:
an implantable pressure sensor configured to ambulatorily sense pulmonary artery pressure from within a patient, the pressure sensor comprising:
a support structure comprising a stabilizing arrangement configured to stabilize the pressure sensor within a pulmonary artery of the patient;
a pressure transducer;
a communications device coupled to the pressure transducer, the communications device configured to effect wireless transmission of a pulmonary artery pressure waveform out of the patient's heart, the pressure transducer and the communications device supported by the support structure; and
an energy source configured to supply power for the pressure transducer and the communications device;
an external cardiac electrical activity sensor configured to sense, using at least one electrode disposed external to the patient, cardiac electrical activity and output a cardiac electrical signal; and
a processor communicatively coupled to the communications device of the pressure sensor and to the external cardiac electrical activity sensor, the processor configured to execute programmed instructions for making a pulmonary artery pressure measurement based at least in part on the cardiac electrical signal and detecting acute pulmonary embolism based on a change in a morphological feature of the pulmonary artery pressure waveform and verifying detection of the acute pulmonary embolism using the cardiac electrical signal.

12. The system of claim 11, comprising a portable patient-external system disposed in a housing configured for handheld manipulation and a patient-external server system, the housing of the portable patient-external system comprising communications circuitry configured to effect wireless communications with the communications device of the pressure sensor and communications with the patient-external server system, the processor disposed in at least one of the housing of the portable patient-external system and the patient-external server system.

13. The system of claim 11, wherein the implantable pressure sensor comprises a charging circuit responsive to an acoustic or inductive signal, the charging circuit generating energy for powering the pressure sensor in response to the acoustic or inductive signal.

14. The system of claim 11, wherein the support structure of the pressure sensor comprises a stent graft configured to radially contract during implantation in the pulmonary artery and expand to stabilize the pressure sensor at an implant site within the pulmonary artery.

15. The system of claim 11, wherein the communications device coupled to the pressure sensor comprises an acoustic communications device.

16. The system of claim 11, wherein the processor is configured to execute programmed instructions for discriminating between acute pulmonary embolism and myocardial infarction based on a change of the pulmonary artery pressure waveform relative to a change in a feature of the cardiac electrical signal.

17. The system of claim 16, wherein the feature of the cardiac electrical signal comprises a feature of an ST segment of the cardiac electrical signal, wherein the processor is configured to execute programmed instructions for detecting myocardial infarction as a change in the ST segment feature and for detecting acute pulmonary embolism as a change in the pulmonary artery pressure measurement in the absence of an appreciable change in the ST segment feature or other myocardial infarction-associated feature of the cardiac electrical signal.

18. The system of claim 11, wherein the processor is configured to execute programmed instructions for discriminating between acute pulmonary embolism and primary pulmonary hypertension based on a rate of change of the pulmonary artery pressure measurement.

19. The system of claim 11, further comprising a sensor configured to sense a parameter indicative of heart failure from within the patient, wherein the processor is configured to execute programmed instructions for discriminating between acute pulmonary embolism and heart failure induced pulmonary hypertension based on a rate of change of the pulmonary artery pressure measurement and a change in the sensed parameter.

20. The system of claim 11, wherein the processor is configured to execute programmed instructions for discriminating between chronic pulmonary embolism and primary pulmonary hypertension based on one or more of a fractional pulse pulmonary artery pressure derived from the pulmonary artery pressure waveform, a coefficient of variation of the pulmonary artery pressure derived from the pulmonary artery pressure waveform, and a fractional time to half the area under the pulmonary artery pressure waveform.

* * * * *